United States Patent [19]

Narwa et al.

[11] Patent Number: 5,919,462
[45] Date of Patent: Jul. 6, 1999

[54] NUCLEIC ACID FRAGMENTS DERIVED FROM THE HIV-1 VIRUS GENOME, CORRESPONDING PEPTIDES AND THEIR APPLICATIONS AS REAGENTS FOR EVALUATION OF THE RISK OF MATERNOFOETAL TRANSMISSION OF HIV-1

[75] Inventors: Remy Narwa, Paris; Pierre Roques, Antony, both of France

[73] Assignee: Commissariat a L'Energie Atomique, Paris, France

[21] Appl. No.: 08/649,991

[22] Filed: May 17, 1996

[30] Foreign Application Priority Data

May 18, 1995 [FR] France ..................................... 9505914

[51] Int. Cl.⁶ .............................. A61K 39/21; C07K 4/02
[52] U.S. Cl. ................................... 424/208.1; 424/187.1; 424/188.1; 424/207.1; 435/7.1; 435/7.92; 435/69.1; 435/69.3; 530/300; 530/326; 530/329
[58] Field of Search ..................................... 530/326, 329, 530/300; 424/187.1, 188.1, 207.1, 208.1; 435/7.1, 7.92, 69.1, 69.3

[56] References Cited

FOREIGN PATENT DOCUMENTS

| 0246829 | 11/1987 | European Pat. Off. . |
|---|---|---|
| 0 284 587 | 9/1988 | European Pat. Off. . |
| 0 426 314 | 5/1991 | European Pat. Off. . |
| WO 87/07906 | 12/1987 | WIPO . |
| WO 90/13564 | 11/1990 | WIPO . |

OTHER PUBLICATIONS

L. Q. Zhang et al., *Journal of Virology*, vol. 67, No. 6, pp. 3345–3356 (1993): Selection for Specific Sequences in the External Envelope Protein of Human Immunodeficiency Virus Type 1 upon Primary Injection.

M. Cornelissen et al., *Journal of Virology*, vol. 69, No. 3, pp. 1810–1818 (1995): Syncytium–Inducing (SI) Phenotype Suppression at Seroconversion after Intramuscular Inoculation of a Non–Syncytium–Inducing/SI Phenotypically Mixed Human Immunodeficiency Virus Population.

*Primary Examiner*—Jeffrey Stucker
*Assistant Examiner*—Phuong T. Bui
*Attorney, Agent, or Firm*—Morgan, Lewis & Bockius LLP

[57] ABSTRACT

This invention provides specific amino acid sequences encoded by nucleic acid fragments derived from the genome of the human immunodeficiency virus type 1 (HIV-1) and to peptides containing such amino acid sequences. The invention further provides immunogenic compositions containing the disclosed amino acid sequences and their associated peptides. The amino acids and peptides of this invention are useful as reagents for the screening, detection and evaluation for the risk of maternofoetal transmission of HIV-1.

16 Claims, 11 Drawing Sheets

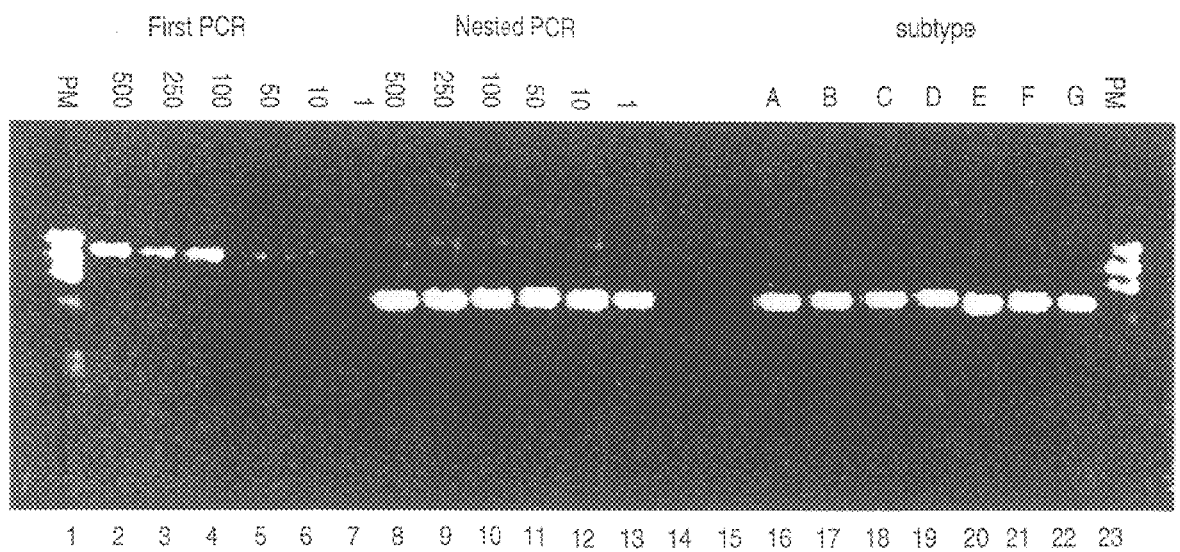

| GENOTYPE | E 12 | V 46 | Q 58 | R 58 | L 61 | E 62 | S 67 | F 75 | R 91 | R 95 | E 102 | M 104 | Q 113 |
|---|---|---|---|---|---|---|---|---|---|---|---|---|---|
| A |  |  | ░ |  |  | ░ |  |  |  |  |  |  |  |
| B | ░ | ░ |  | ░ | ░ |  | ░ |  | ░ |  |  |  |  |
| G |  |  |  |  |  |  |  |  |  | ░ | ░ |  | ░ |
| D |  |  |  |  |  |  |  | ░ |  |  |  | ░ |  |

PEPTIDE

| TRANSMITTED | NON-TRANSMITTED | CONTROLS |
|---|---|---|
| 1  2 | 3  4  5  6 | 7  8 |

FIG. 7A

| SEQ ID N° | Group | | | | sequence | | | | |
|---|---|---|---|---|---|---|---|---|---|
| | consensus | | *LysGluAla | LeuGluLys | LeuGluGlu | leGluGluGl | uGlnAsnLys | SerLysLysl | ysAla |
| | A | | | non-transmitted | | | | | |
| 4 | | | *LysGluAla | LeuAspLys | leGluGlul | leGluGlul | eGlnLysLys | SerLysGlnL | ysAla |
| 5 | BAB_MNT | | *AAGGAAGCC | TTAGATAAAA | TAGAGGAAAT | TAGAGGAAAT | ACAAAAGAAG | AGCAAGCAAA | AGACA |
| 6 | DOS_MNT | | *AAGGAAGCT | TTAGATAAAT | TAGAGGAAAT | TAGAGGAAAT | ACAAAATAAG | AGCAAACAAA | AGACA |
| 7 | LAN_MNT | | *AAGGAAGCC | TTAGATAAGC | TGGAGGAAAT | TAGAGGAAAT | ACACATAAG | AACAAGCAAA | AGGCA |
| 8 | FRA_MNT | | *AAGGAAGCC | TTAGATAAAA | TAGAGGAGAT | TAGAGGAAAT | ACAAATAAG | AGCAAGCAAA | AAACA |
| | WAN_MNT | | *AAGGAAGCT | TTAGATAAAA | TAGAGGAACT | TAGAGGAAGT | ACAAAAGAAG | AGTAAGCAAA | AAGCA |
| | A | | | transmitted | | | | | |
| 1 | DIA_MT | | *AAAGAAGCT | TTAGATAAAA | TAGAGGAAAT | TAGAGGAAAT | ACAAAAAAGG | AGCGGGCAAA | AGACA |
| | DIA_C | | *AAAGAAGCT | TTAGATAAAA | TAGAGGAAAT | TAGAGGAAAT | ACAAAAAAGG | AGCGGGCAAA | AGACA |
| 2 | MAM_MT | | *AAAGAAGCT | TTAGACAAAA | TAGAGGAAAT | TAGAGGAAGT | ACAAAGTAAG | AACAAGCAAA | AGGCA |
| 117 | MAM_C | | *AAAGAAGCC | TTAGATNAAN | TAGAGGANAT | TAGAGGAAAT | ACAAAAAAGG | AGCGGGCAAA | AGACA |
| 3 | MOU_MT | | *AAAGAAGCT | TTAGATAAAA | TAGAGGAAGT | TAGAGGAAGT | ACAGAAAAAG | AGCAAGCAAA | AGACA |
| 118 | MOU_C | | *AAAGAAGCT | TTAGATAAAA | TAGAGGAAGT | TAGAGGAAGT | ACAGAGAAAG | AGCAAGCAAA | AGACA |
| | B | | | non-transmitted | | | | | |
| | | | *LysGluAla | LeuGluLysV | alGluGluGl | uGlnAsnLys | SerLysLys | SerLysLysl | ysAla |
| 17 | FAL_MNT | | *AAGGAAGCT | TTAGAGAAGA | TAGAGGAAGA | GCAAAACAAA | AGTAAGAAAA | AAGCA | |
| 18 | HAR_MNT | | *AAGGAAGCT | CTAGAGAAGG | TAGAGGAAGA | GCAAAACAAA | AGTAAGAAAA | ANGCA | |
| 119 | HMI_MNT | | *AAGGAAGCT | TTAGAGAAGA | TAGAGGAAGA | GCAAAACAAA | AGTAAGAAAA | AAGCA | |
| 120 | LOUB_MNT | | *AAGGAAGCT | CTAGAGAAGG | TAGAGGAAGA | GCAAAACAAA | AGTAAGAAAA | AAGCA | |
| 19 | RIV_MNT | | *AAGGAAGCT | TTAGACAAGA | TAGAGGAAGA | ACAAAACAAA | AGTAAGAAAA | AAGCA | |
| 18 | VIL_MNT | | *AAGGAAGCT | CTAGAGAAGG | TAGAGGAAGA | GCAAAACAAA | AGTAAGAAAA | ANGCA | |
| 20 | CHEI_MNT | | *AAGGAAGCT | CTAGAGAAGA | TAGAGGAAGA | GCAAAACAAA | AGTAAGAAAA | AGGCA | |
| 21 | CEL_MNT | | *AAGGAAGCT | TTAGAGAAGG | TAGAGGAAGA | GCAAAACCAA | AGTAAGAGAA | AAGCA | |
| 22 | SIM_MNT | | *AAGGAAGCT | CTAGACAAGA | TAGAGGAAGA | GCAAAACAAA | AGTAAGAAAA | AGGCA | |
| 23 | MOE_MNT | | *AAGGAAGCT | TTAGAGAAGA | TAGAGGAAGA | GCAAAACAAA | AGTAAGAAAA | AAGCC | |
| 24 | GOB_MNT | | *AAGGAAGCT | TTAGAGAAGA | TAGAGGAAGA | NCAAAACAAA | AGTAAGAAAA | AGGCA | |
| 17 | BAR_MNT | | *AAGGAAGCT | TTAGAGAAGG | TAGAGGAAGA | GCAAAACAAA | AGTAAGAAAA | AGGCA | |
| 25 | 4541_MNT | | *AAGGAAGCT | TTAGAGAAAG | TAGAGGAAGA | GCAAAACAAA | AGTAAGAAAA | AAGCA | |
| 26 | 2754_MNT | | *AAGGAAGCT | TTAGAGAAGG | TAGAGGAAGA | GCAAAACAAA | AGTAAGAAAA | AGGCA | |
| 121 | 5613_MNT | | *AAGGAAGCT | TTAGAGAAGA | TAGAGGAAGA | GCAAAACAAA | AGTAAGAAAA | AAGCA | |
| 27 | 2826_MNT | | *AAGGAAGCT | TTAGAGAAGA | TAGAGGAAGA | GCAAAACAAG | AGTAAGAAAA | AAGCA | |

FIG. 7B

| | | | *LysGluAla | LeuGluLysI | transmitted LeuGluLysi | leGluGluGl | uGlnAsnLys | SerLysLysL | ysAla |
|---|---|---|---|---|---|---|---|---|---|
| B | | | *LysGluAla | LeuGluLysI | leGluGluGl | uGlnAsnLys | SerLysLysL | ysAla | |
| | ABD_MT | 9 | *AAGGAAGCT | TTAGATAAGA | TAGAGGAAGA | ACAAAACAAA | AGTAAGAAAA | AAGCA | |
| | ABD_C | | *AAGGAAGCT | TTAGATAAGA | TAGAGGAAGA | ACAAAACAAA | AGTAAGAAAA | AAGCA | |
| | ARI_MT | 10 | *AAGGAAGCT | TTAGATAAGA | TAGAGGAAGA | GCAAAACAAA | AGTAAGAAAA | AAGCA | |
| | ARI_C | | *AAGGAAGCT | TTAGATAAGA | TAGAGGAAGA | GCAAAACAAA | AGTAAGAAAA | AAGCA | |
| | BOI_MT | 11 | *AAGGAAGCT | TTAGAGAAGA | TAGAGGAAGA | GCAAAACAAA | AGTAAGAAAA | AGGCA | |
| | BOI_C | 122 | *AAGGAAGCT | TTAGAGAAGA | TAGAGGAAGA | GCAAAACAAA | AGTAAGAAAA | AGGCA | |
| | DUM_MT | 12 | *AAGGAAGCT | TTAGAGAAGA | TAGAGGAAGA | GCAAAACAAA | AGTAAGAAAA | AAGCA | |
| | DUM_C | | *AAGGAAGCT | TTAGAGAAGA | TAGAGGAAGA | GCAAAACAAA | AGTAAGAAAA | AAGCA | |
| | LEN_MT | 12 | *AAGGAAGCT | TTAGAGAAGA | TAGAGGAAGA | GCAAAACAAA | AGTAAGAAAA | AAGCA | |
| | LEN_C | 123 | *AAGGAAGCT | TTAGAGAAGA | TAGAGGAAGA | GCAAAACAAA | AGTAAGAAAA | AAGCA | |
| | PAL_MT | 13 | *AAGGAAGCT | TTAGAAAAGA | TAGAGGAAGA | GCAAAACAAA | AGTAAGAAAA | AAGCN | |
| | PAL_C | 124 | *AAGGAAGCT | TTAGATAAGA | TAGAGGAAGA | GCAAAACAAA | AGTAAGAAAA | AAGCA | |
| | RYO_MT | 14 | *AAGGAAGCT | TTAGACAAGA | TAGAGGAAGA | GCAAAACAAA | AGTAAGAAAA | AAGCA | |
| | RYO_C | 125 | *AAGGAAGCT | TTAGACAAGA | TAGAGGAAGA | GCAAAACAAA | AGTAAGGAAA | AAGCA | |
| | FLO_MT | 15 | *AAGGAAGCT | TTAGAGAAGA | TAGAAGGAAGA | GCAAAACAAA | AGTAAGGAAA | CAAGC | |
| | FLO_C | | *AAGGAAGCT | TTAGAGAAGA | TAGAGGAAGA | GCAAAACAAA | AGTAAGGAAA | CAAGC | |
| | LIN_C | 126 | *AAGGAAGCT | TTAGAGAAGA | TAGAGGAAGA | GCAAAACAAA | AGTAAGGAAA | AGGCA | |
| | AMO_C | 127 | *AAGGAAGCC | TTAGAGAAGA | TAGAGGAAGA | GCAAAACAAA | AGTAAGGAAA | AAGCA | |
| | 4538_MT | 12 | *AAGGAAGCT | TTAGAGAAGA | TAGAGGAAGA | GCAAAACAAA | AGTAAGAAAA | AAGCA | |
| | 4501_MT | 16 | *AAGGAAGCT | TTAGAGAAGA | TAGAGGAAGA | GCAAAACAAA | AGTAAGAAAAC | AAGCA | |
| | 2758_MT | 128 | *AAGGAAGCT | TTAGATAAGA | TAGAGGAAGA | GCAAAACAAA | AGTAAGAAAA | AAGCA | |
| | 2530_MT | 129 | *AAGGAAGCT | TTAGATAAGN | TAGAGGAAGA | GCAAAACAAA | AGTAAGAAAA | AGGAA | |
| G | | | *LysGluAla | LeuGluLysV | alGluLysAr | gGlnLysIle | SerGlnGlnL | ysIle | |
| | MPA_M | 28 | *AAAGAAGCT | CTAGAGGAAG | TGAAAAGAG | ACAAAAGATC | AGTCAGCAAA | AAATA | |
| | MPA_C | 130 | *AAAGAAGCT | CTAGAGGAAG | TGAAAAGAG | ACAAAAGAAC | AGTCAGCAAA | AAATA | |
| | DUB_C | 28 | *AAAGAAGCT | CTAGAGGAAG | TGAAAAGAG | ACAAAAGATC | AGTCAGCAAA | AAATA | |
| | IGN_C | 29 | *AAAGAAGCT | CTAGAGGAAG | TGAAAAGAG | ACAAAAGAAA | AGTCAGCAAA | AAATA | |
| | OSA_MT | 30 | *AAAGAAGCT | CTAGAGGAAG | TGAAAAGGT | ACGAAAAAAC | AAGCAGCAAA | AAGCA | |
| B | | | *LysGluAla | LeuGluLysM | etGluGluGl | uGlnAsnLys | SerLysLysL | ysAla | |
| | BOU | 31 | *AAGGAAGCT | TTAGAGAAGA | TGGAGGAAGA | GCAAAACAAA | AGTAAGAAGA | AAGCA | |

SEQUENCE LISTING (1) GENERAL INFORMATION:

(iii) NUMBER OF SEQUENCES: 130

(2) INFORMATION FOR SEQ ID NO:1:

(i) SEQUENCE CHARACTERISTICS:
           (A) LENGTH: 54 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:1:

AAAGAAGCTT TAGATAAAAT AGAGGAAATA CAAAAAAGGA GCGGGCAAAA GACA          54

(2) INFORMATION FOR SEQ ID NO:2:

(i) SEQUENCE CHARACTERISTICS:
           (A) LENGTH: 54 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:2:

AAAGAAGCCT TAGACAAAAT AGAGGAAATA CAAAGTAAGA ACAAGCAAAA GGCA          54

(2) INFORMATION FOR SEQ ID NO:3:

(i) SEQUENCE CHARACTERISTICS:
           (A) LENGTH: 54 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:3:

AAGGAAGCTT TAGATAAAAT AGAGGAAGTA CAGAAAAAGA GCAAGCAAAA GACA          54

(2) INFORMATION FOR SEQ ID NO:4:

(i) SEQUENCE CHARACTERISTICS:
           (A) LENGTH: 54 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:4:

AAGGAAGCCT TAGATAAAAT AGAGGAAATA CAAAAGAAGA GCAAGCAAAA GACA          54

(2) INFORMATION FOR SEQ ID NO:5:

(i) SEQUENCE CHARACTERISTICS:
           (A) LENGTH: 54 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:5:

AAGGAAGCTT TAGATAAATT AGAGGAAATA CAAAATAAGA GCAAACAAAA GACA          54

(2) INFORMATION FOR SEQ ID NO:6:

(i) SEQUENCE CHARACTERISTICS:
           (A) LENGTH: 54 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:6:

AAGGAAGCTT TAGATAAGCT GGAGGAAATA CAACATAAGA ACAAGCAAAA GACA    54

(2) INFORMATION FOR SEQ ID NO:7:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AAGGAAGCCT TAGATAAAAT AGAGGAGATA CAAAATAAGA GCAAGCAAAA AACA    54

(2) INFORMATION FOR SEQ ID NO:8:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AAGGAAGCTT TAGATAAAAT AGAGGAACTA CAAAAGAAGA GTAAGCAAAA AGCA    54

(2) INFORMATION FOR SEQ ID NO:9:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

AAGGAAGCTT TAGATAAGAT AGAGGAAGAA CAAAACAAAA GTAAGAAAAA AGCA    54

(2) INFORMATION FOR SEQ ID NO:10:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AAGGAAGCTT TAGATAAGAT AGAGGAAGAG CAAAACAAAA GTAAGAAAAA AGCA    54

(2) INFORMATION FOR SEQ ID NO:11:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AAGGAAGCTT TAGAGAAGAT AGAGGAAGAG CAAAACAAAA GTAAGAAAAA GGCA    54

(2) INFORMATION FOR SEQ ID NO:12:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AAGGAAGCTT TAGAGAAGAT AGAGGAAGAG CAAAACAAAA GTAAGAAAAA AGCA    54

(2) INFORMATION FOR SEQ ID NO:13:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

AAGGAAGCTT TAGATAAGAT AGAGGAAGAG CAAAACAAAA GTAAGAAAAA AGCA    54

(2) INFORMATION FOR SEQ ID NO:14:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

AAGGAAGCTT TAGACAAGAT AGAAGAAGAG CAAAACAAAA GTAAGAAAAA AGCA    54

(2) INFORMATION FOR SEQ ID NO:15:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

AAGGAAGCTT TAGAGAAGAT AGAGGAAGAG CAAAACAAAA GTAAGAAAAC AAGC    54

(2) INFORMATION FOR SEQ ID NO:16:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

AAGGAAGCTT TAGAGAAGAT AGAGGAAGAG CAAAACAAAA GTAAGAAACA AGCA    54

(2) INFORMATION FOR SEQ ID NO:17:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:17:

AAGGAAGCTT TAGAGAAGAT AGAGGAAGAG CAAAACAAAA GTAAGAAAAA AGCA            54

(2) INFORMATION FOR SEQ ID NO:18:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

AAGGAAGCTC TAGAGAAGGT AGAGGAAGAG CAAAACAAAA GTAAGAAAAA NGCA            54

(2) INFORMATION FOR SEQ ID NO:19:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

AAGGAAGCTT TAGACAAGAT AGAGGAAGAA CAAAACAAAA GTAAGAAAAA AGCA            54

(2) INFORMATION FOR SEQ ID NO:20:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

AAGGAAGCTT TAGAGAAGAT AGAGGAAGAG CAAAACAAAA GTAAGAAAAA GGCA            54

(2) INFORMATION FOR SEQ ID NO:21:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

AAGGAAGCTT TAGAGAAGGT AGAGGAAGAG CAAACCAAAA GTAAGAGAAA AGCA            54

(2) INFORMATION FOR SEQ ID NO:22:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

AAGGAAGCTC TAGACAAGAT AGAGGAAGAG CAAAACAAAA GTAAGAAAAA GGCA        54

(2) INFORMATION FOR SEQ ID NO:23:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

AAGGAAGCTT TAGACAAGAT AGAGGAAGAG CAAACCAAAA GTAAGAAAAA AGCA        54

(2) INFORMATION FOR SEQ ID NO:24:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

AAGGAAGCTT TAGAGAAGAT AGAGGAAGAN CAAACCAAAA GTAAGAAAAA AGCA        54

(2) INFORMATION FOR SEQ ID NO:25:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

AAGGAAGCTT TAGAGAAAGT AGAGGAAGAG CAAAACAAAA GTAAGAAAAA GGCA        54

(2) INFORMATION FOR SEQ ID NO:26:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

AAGGAAGCTT TAGAGAAGGT AGAGGAAGAG CAAAACAAAA GTAAGAAAAA AGCA        54

(2) INFORMATION FOR SEQ ID NO:27:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
AAGGAAGCTT TAGAGAAGAT AGAGGAAGAG CAAAACAAGA GTAAGAAAAA AGCA           54
```

(2) INFORMATION FOR SEQ ID NO:28:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
AAAGAAGCTC TAGAGGAAGT GGAAAAGAGA CAAAAGATCA GTCAGCAAAA AATA           54
```

(2) INFORMATION FOR SEQ ID NO:29:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

```
AAAGAAGCTC TAGAGGAAGT GGAAAAGAGA CAAAAGATCA GTCAGAAAAA AATA           54
```

(2) INFORMATION FOR SEQ ID NO:30:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
AAAGAAGCTC TAGAGGAAGT GGAAAAGGTA CGAAAAAACA AGCAGCAAAA AGCA           54
```

(2) INFORMATION FOR SEQ ID NO:31:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

```
AAGGAAGCTT TAGAGAAGAT GGAGGAAGAG CAAAACAAAA GTAAGAAAAA AGCA           54
```

(2) INFORMATION FOR SEQ ID NO:32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:32:

```
TTTTGTTTTG CTCTTCCTCT ATCTT                                          25
```

(2) INFORMATION FOR SEQ ID NO:33:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "probe"

(xi) SEQUENCE DESCRIPTION: SEQ ID NO:33:

GTTTTGCTCT TCCTCTACC                                                19

(2) INFORMATION FOR SEQ ID NO:34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:34:

GGTTTGCTCT TCCTCTATC                                                19

(2) INFORMATION FOR SEQ ID NO:35:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:35:

GTTTGCTCTT CCTCTACCT                                                19

(2) INFORMATION FOR SEQ ID NO:36:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

Lys Glu Ala Leu Asp Lys Ile Glu Glu Ile Gln Lys Arg Ser Gly Gln
1               5                   10                  15

Lys Thr (2) INFORMATION FOR SEQ ID NO:37:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

Lys Glu Ala Leu Asp Lys Ile Glu Glu Ile Gln Ser Lys Asn Lys Gln
1               5                   10                  15

Lys Ala (2) INFORMATION FOR SEQ ID NO:38:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

```
Lys Glu Ala Leu Asp Lys Ile Glu Glu Val Gln Lys Lys Ser Lys Gln
1               5                   10                  15
Lys Thr
```

(2) INFORMATION FOR SEQ ID NO:39:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

```
Lys Glu Ala Leu Asp Lys Ile Glu Glu Ile Gln Lys Lys Ser Lys Gln
1               5                   10                  15
Lys Thr
```

(2) INFORMATION FOR SEQ ID NO:40:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

```
Lys Glu Ala Leu Asp Lys Leu Glu Glu Ile Gln Asn Lys Ser Lys Gln
1               5                   10                  15
Lys Thr
```

(2) INFORMATION FOR SEQ ID NO:41:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

```
Lys Glu Ala Leu Asp Lys Leu Glu Glu Ile Gln His Lys Asn Lys Gln
1               5                   10                  15
Lys Thr
```

(2) INFORMATION FOR SEQ ID NO:42:

(i) SEQUENCE CHARACTERISTICS:
        (A) LENGTH: 18 amino acids
        (B) TYPE: amino acid (C) STRANDEDNESS:
        (D) TOPOLOGY: linear (ii) MOLECULE TYPE: peptide (xi) SEQUENCE DESCRIPTION: SEQ ID NO:42:

Lys Glu Ala Leu Asp Lys Ile Glu Glu Ile Gln Asn Lys Ser Lys Gln
    1               5                   10                  15

Lys Thr (2) INFORMATION FOR SEQ ID NO:43:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

Lys Glu Ala Leu Asp Lys Ile Glu Glu Leu Gln Lys Lys Ser Lys Gln
    1               5                   10                  15

Lys Ala (2) INFORMATION FOR SEQ ID NO:44:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

Lys Glu Ala Leu Asp Lys Ile Glu Glu Glu Gln Asn Lys Ser Lys Lys
    1               5                   10                  15

Lys Ala (2) INFORMATION FOR SEQ ID NO:45:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:45:

Lys Glu Ala Leu Glu Lys Ile Glu Glu Glu Gln Asn Lys Ser Lys Lys
    1               5                   10                  15

Lys Ala (2) INFORMATION FOR SEQ ID NO:46:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:46:

```
Lys Glu Ala Leu Glu Lys Ile Glu Glu Glu Gln Asn Lys Ser Lys Lys
 1               5                  10                  15

Gln Ala
```

(2) INFORMATION FOR SEQ ID NO:47:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:47:

```
Lys Glu Ala Leu Glu Lys Val Glu Glu Glu Gln Asn Lys Ser Lys Lys
 1               5                  10                  15

Lys Ala
```

(2) INFORMATION FOR SEQ ID NO:48:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:48:

```
Lys Glu Ala Leu Glu Lys Val Glu Glu Glu Gln Thr Lys Ser Lys Arg
 1               5                  10                  15

Lys Ala
```

(2) INFORMATION FOR SEQ ID NO:49:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:49:

```
Lys Glu Ala Leu Glu Lys Ile Glu Glu Glu Gln Asn Lys Ser Glu Lys
 1               5                  10                  15

Lys Ala
```

(2) INFORMATION FOR SEQ ID NO:50:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:50:

```
Lys Glu Ala Leu Asp Lys Ile Glu Glu Glu Gln Thr Lys Ser Lys Lys
 1               5                  10                  15

Lys Ala
```

(2) INFORMATION FOR SEQ ID NO:51:

(i) SEQUENCE CHARACTERISTICS:
    (A) LENGTH: 18 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:51:

Lys Glu Ala Leu Glu Lys Ile Glu Glu Gln Thr Lys Ser Lys Lys
1               5                   10                  15

Lys Ala (2) INFORMATION FOR SEQ ID NO:52:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:52:

Lys Glu Ala Leu Glu Glu Val Glu Lys Arg Gln Lys Ile Ser Gln Gln
1               5                   10                  15

Lys Ile (2) INFORMATION FOR SEQ ID NO:53:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:53:

Lys Glu Ala Leu Glu Glu Val Glu Lys Arg Gln Lys Lys Ser Lys Gln
1               5                   10                  15

Lys Ile (2) INFORMATION FOR SEQ ID NO:54:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:54:

Lys Glu Ala Leu Glu Glu Val Glu Lys Val Arg Lys Asn Lys Gln Gln
1               5                   10                  15

Lys Ala (2) INFORMATION FOR SEQ ID NO:55:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:55:

Lys Glu Ala Leu Glu Lys Met Glu Glu Glu Gln Asn Lys Ser Lys Lys
1               5                   10                  15

Lys Ala (2) INFORMATION FOR SEQ ID NO:56:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:56:

TTTTGTTTTG CTCTTCCTCT ACTTT                                      25

(2) INFORMATION FOR SEQ ID NO:57:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:57:

CTTTTGTTTT GCTCTTCTTC TATCT                                      25

(2) INFORMATION FOR SEQ ID NO:58:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:58:

ACTCTGGTAG CTAGAGATCC CT                                        22

(2) INFORMATION FOR SEQ ID NO:59:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:59:

GGTGATATGG CCTGATGTAC CAT                                       23

(2) INFORMATION FOR SEQ ID NO:60:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
    (A) DESCRIPTION: /desc = "primer"

(xi) SEQUENCE DESCRIPTION: SEQ ID NO:60:

TTTGGTCCTT GTCTTATGTC CAGAATGC                                          28

(2) INFORMATION FOR SEQ ID NO:61:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:61:

Xaa Xaa Glu Xaa Xaa Xaa Xaa
    1               5

(2) INFORMATION FOR SEQ ID NO:62:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:62:

Met Gly Ala Arg Ala Ser Val Leu Ser Gly Gly Glu Leu Asp Arg Trp
    1               5                   10                  15

Glu Lys Ile Arg Leu Arg Pro Gly Gly Lys Lys Lys Tyr Arg Leu Lys
                    20                  25                  30

His Ile Val Trp Ala Ser Arg Glu Leu Glu Arg Phe Ala Val Asn Pro
                35                  40                  45

Gly Leu Leu Glu Thr Ser Glu Gly Cys Arg Gln Ile Leu Gly Gln Leu
        50                  55                  60

Gln Pro Ser Leu Gln Thr Gly Ser Glu Glu Leu Arg Ser Leu Phe Asn
    65                  70                  75                  80

Thr Val Ala Thr Leu Tyr Cys Val His Gln Lys Ile Asp Val Lys Asp
                    85                  90                  95

Thr Lys Glu Ala Leu Glu Lys Ile Glu Glu Gln Asn Lys Ser Lys
                100                 105                 110

Lys Lys Ala Gln Gln Ala Ala Ala Gly Thr Gly Asn Ser Ser Gln Val
                115                 120                 125

Ser Gln Asn Tyr
        130

(2) INFORMATION FOR SEQ ID NO:63:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:63:

Met Gly Ala Arg Ala Ser Val Leu Ser Gly Gly Lys Leu Asp Ala Trp
    1               5                   10                  15

```
        Glu  Lys  Ile  Arg  Leu  Arg  Pro  Gly  Gly  Lys  Lys  Tyr  Arg  Leu  Lys
                       20                       25                       30

His  Ile  Val  Trp  Ala  Ser  Arg  Glu  Leu  Glu  Arg  Phe  Ala  Leu  Asn  Pro
                       35                       40                       45

Gly  Leu  Leu  Glu  Ser  Ala  Glu  Gly  Cys  Gln  Gln  Leu  Met  Glu  Gln  Leu
                  50                       55                       60

Gln  Ser  Thr  Leu  Lys  Thr  Gly  Ser  Glu  Glu  Ile  Lys  Ser  Leu  Tyr  Asn
        65                       70                       75                       80

Thr  Ile  Ala  Thr  Leu  Trp  Cys  Val  His  Gln  Arg  Met  Glu  Ile  Arg  Asp
                            85                       90                       95

Thr  Lys  Glu  Ala  Leu  Asp  Lys  Ile  Glu  Glu  Ile  Gln  Lys  Lys  Ser  Lys
                            100                      105                      110

Gln  Lys  Thr  Gln  Gln  Ala  Ala  Ala  Thr  Gly  Ser  Ser  Ser  Gln  Val
                       115                      120                      125

Ser  Gln  Asn  Tyr
                  130
```

(2) INFORMATION FOR SEQ ID NO:64:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:64:

```
        Met  Gly  Ala  Arg  Ala  Ser  Val  Leu  Ser  Gly  Gly  Lys  Leu  Asp  Ala  Trp
        1                 5                       10                       15

Glu  Lys  Ile  Arg  Leu  Arg  Pro  Gly  Gly  Lys  Lys  Tyr  Arg  Leu  Lys
                       20                       25                       30

His  Leu  Val  Trp  Ala  Ser  Arg  Glu  Leu  Glu  Arg  Phe  Ala  Leu  Asn  Pro
                       35                       40                       45

Gly  Leu  Leu  Glu  Thr  Gly  Glu  Gly  Cys  Gln  Gln  Leu  Met  Glu  Gln  Leu
                  50                       55                       60

Gln  Ser  Thr  Leu  Arg  Thr  Gly  Ser  Glu  Glu  Leu  Lys  Ser  Leu  Phe  Asn
        65                       70                       75                       80

Thr  Ile  Ala  Thr  Leu  Trp  Cys  Val  His  Gln  Arg  Ile  Asp  Ile  Lys  Asp
                            85                       90                       95

Thr  Lys  Glu  Ala  Leu  Asp  Lys  Leu  Glu  Glu  Ile  Gln  Asn  Lys  Ser  Gln
                            100                      105                      110

Lys  Lys  Thr  Gln  Gln  Ala  Ala  Ala  Thr  Gly  Ser  Ser  Ser  Gln  Val
                       115                      120                      125

Ser  Gln  Asn  Tyr
                  130
```

(2) INFORMATION FOR SEQ ID NO:65:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:65:

```
        Met  Gly  Ala  Arg  Ala  Ser  Val  Leu  Ser  Gly  Gly  Lys  Leu  Asp  Ala  Trp
        1                 5                       10                       15
```

```
     Glu Lys Ile Arg Leu Arg Pro Gly Gly Lys Lys Tyr Arg Leu Lys
                  20                  25                  30

His Leu Val Trp Ala Ser Arg Glu Leu Asp Arg Phe Ala Leu Asn Pro
                      35                  40                  45

Gly Leu Leu Glu Thr Ala Glu Gly Cys Gln Gln Ala Ile Glu Gln Leu
                  50                  55                  60

Gln Pro Ser Ile Lys Thr Gly Ser Glu Leu Lys Ser Leu Phe Asn
     65                  70                  75                  80

Ala Ile Ala Thr Leu Trp Cys Val His Gln Arg Ile Glu Val Arg Asp
                      85                  90                  95

Thr Lys Glu Ala Leu Asp Lys Leu Glu Glu Ile Gln His Lys Asn Lys
                      100                 105                 110

Gln Lys Thr Gln Gln Val Ala Ser Asn Thr Gly Ser Ser Asn Lys Val
                      115                 120                 125

Ser Gln Asn Tyr
                 130

(2) INFORMATION FOR SEQ ID NO:66:

(i) SEQUENCE CHARACTERISTICS:
         (A) LENGTH: 132 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:66:

Met Gly Ala Arg Ala Ser Val Leu Ser Gly Gly Lys Leu Asp Ala Trp
     1               5                   10                  15

Glu Lys Ile Arg Leu Arg Pro Gly Gly Lys Lys Tyr Arg Met Lys
                      20                  25                  30

His Leu Val Trp Ala Ser Arg Glu Leu Glu Arg Phe Ala Leu Asn Pro
                      35                  40                  45

Gly Leu Leu Glu Thr Thr Glu Gly Cys Gln Gln Ile Ile Glu Gln Leu
                  50                  55                  60

Gln Pro Ala Leu Arg Thr Gly Thr Glu Glu Leu Arg Ser Leu Tyr Asn
     65                  70                  75                  80

Thr Val Ala Thr Leu Tyr Cys Val His Lys Arg Ile Glu Ile Lys Asp
                      85                  90                  95

Thr Lys Glu Ala Leu Asp Lys Ile Glu Glu Ile Gln Asn Lys Ser Lys
                      100                 105                 110

Gln Lys Thr Gln Gln Ala Ala Ala Asp Thr Gly Asn Ser Asn Lys Val
                      115                 120                 125

Ser Gln Asn Tyr
                 130

(2) INFORMATION FOR SEQ ID NO:67:

(i) SEQUENCE CHARACTERISTICS:
         (A) LENGTH: 132 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:67:

Met Gly Xaa Arg Ala Ser Val Leu Ser Gly Gly Lys Leu Asp Ser Trp
     1               5                   10                  15
```

```
        Glu  Lys  Ile  Arg  Leu  Arg  Pro  Gly  Gly  Lys  Lys  Tyr  Arg  Met  Lys
                       20                       25                       30

His  Leu  Val  Trp  Ala  Ser  Arg  Glu  Leu  Asp  Arg  Phe  Ala  Leu  Asn  Pro
                       35                       40                       45

Gly  Leu  Leu  Glu  Thr  Ala  Glu  Gly  Cys  Gln  Gln  Ile  Leu  Glu  Gln  Ile
                       50                       55                       60

Gln  Pro  Ala  Leu  Lys  Thr  Gly  Ser  Glu  Xaa  Leu  Arg  Ser  Leu  Tyr  Asn
        65                       70                       75                       80

Thr  Val  Ala  Thr  Leu  Tyr  Cys  Val  His  Gln  Arg  Ile  Asp  Val  Lys  Asp
                            85                       90                       95

Thr  Lys  Glu  Ala  Leu  Asp  Lys  Ile  Glu  Glu  Leu  Gln  Lys  Lys  Ser  Lys
                       100                      105                      110

Gln  Lys  Ala  Gln  Gln  Ala  Ala  Ala  Asp  Thr  Gly  Asn  Asn  Lys  Gln  Val
                       115                      120                      125

Ser  Gln  Asn  Tyr
                       130

(2)  INFORMATION FOR SEQ ID NO:68:

(i)  SEQUENCE CHARACTERISTICS:
          (A)  LENGTH: 132 amino acids
          (B)  TYPE: amino acid
          (C)  STRANDEDNESS:
          (D)  TOPOLOGY: linear (ii)  MOLECULE TYPE: peptide (xi)  SEQUENCE DESCRIPTION: SEQ ID NO:68:

Met  Gly  Ala  Arg  Ala  Ser  Val  Leu  Ser  Gly  Gly  Lys  Leu  Asp  Ala  Trp
        1                   5                       10                       15

Glu  Lys  Ile  Arg  Leu  Arg  Pro  Gly  Gly  Lys  Lys  Tyr  Arg  Leu  Lys
                       20                       25                       30

His  Leu  Val  Trp  Ala  Ser  Arg  Glu  Leu  Glu  Arg  Phe  Ala  Leu  Asn  Pro
                       35                       40                       45

Ser  Leu  Leu  Glu  Thr  Thr  Glu  Gly  Cys  Gln  Gln  Ile  Met  Glu  Gln  Leu
                       50                       55                       60

Gln  Ser  Ala  Leu  Arg  Thr  Gly  Thr  Glu  Glu  Leu  Arg  Ser  Leu  Tyr  Asn
        65                       70                       75                       80

Thr  Val  Ala  Thr  Leu  Tyr  Cys  Val  His  Gln  Arg  Ile  Glu  Ile  Lys  Asp
                            85                       90                       95

Thr  Lys  Glu  Ala  Leu  Asp  Lys  Ile  Glu  Glu  Ile  Gln  Lys  Arg  Ser  Gly
                       100                      105                      110

Gln  Lys  Thr  Gln  Gln  Ala  Ala  Ala  Asp  Thr  Gly  Asn  Asn  Lys  Gln  Val
                       115                      120                      125

Ser  Gln  Asn  Tyr
                       130

(2)  INFORMATION FOR SEQ ID NO:69:

(i)  SEQUENCE CHARACTERISTICS:
          (A)  LENGTH: 132 amino acids
          (B)  TYPE: amino acid
          (C)  STRANDEDNESS:
          (D)  TOPOLOGY: linear (ii)  MOLECULE TYPE: peptide (xi)  SEQUENCE DESCRIPTION: SEQ ID NO:69:

Met  Gly  Ala  Arg  Ala  Ser  Val  Leu  Ser  Gly  Gly  Lys  Leu  Asp  Ala  Trp
        1                   5                       10                       15
```

```
        Glu Lys Ile Arg Leu Arg Pro Gly Gly Lys Lys Tyr Arg Leu Lys
                    20                  25                  30

His Leu Val Trp Ala Ser Arg Glu Leu Glu Arg Phe Ala Leu Asn Pro
                    35                  40                  45

Ser Leu Leu Glu Thr Thr Glu Gly Cys Gln Gln Ile Met Glu Gln Leu
         50                  55                  60

Gln Ser Ala Leu Arg Thr Gly Thr Glu Glu Leu Arg Ser Leu Tyr Asn
         65                  70                  75                  80

Thr Val Ala Thr Leu Tyr Cys Val His Gln Arg Ile Glu Ile Lys Asp
                        85                  90                  95

Thr Lys Glu Ala Leu Asp Lys Ile Glu Glu Ile Gln Lys Arg Ser Gly
                    100                 105                 110

Gln Lys Thr Gln Gln Ala Ala Ala Asp Thr Gly Asn Asn Lys Gln Val
                    115                 120                 125

Ser Gln Asn Tyr
            130

(2) INFORMATION FOR SEQ ID NO:70:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:70:

Met Gly Ala Arg Ala Ser Val Leu Ser Gly Gly Lys Leu Asp Ala Trp
         1               5                  10                  15

Glu Arg Ile Arg Leu Arg Pro Gly Gly Lys Lys Thr Tyr Arg Leu Lys
                    20                  25                  30

His Leu Val Trp Ala Ser Arg Glu Leu Glu Arg Phe Ala Leu Asn Pro
                    35                  40                  45

Gly Leu Leu Glu Thr Ala Glu Gly Cys Gln Gln Leu Met Glu Gln Leu
         50                  55                  60

Gln Ser Ala Leu Lys Thr Gly Ser Glu Glu Leu Lys Ser Leu Tyr Asn
         65                  70                  75                  80

Thr Leu Ala Thr Leu Trp Cys Val His Gln Arg Ile Asp Val Lys Asp
                        85                  90                  95

Thr Lys Glu Ala Leu Asp Lys Ile Glu Glu Ile Gln Ser Lys Asn Lys
                    100                 105                 110

Gln Lys Ala Gln Gln Ala Ala Ala Ala Thr Gly Asn Asn Ser Asn Leu
                    115                 120                 125

Ser Gln Asn Tyr
            130

(2) INFORMATION FOR SEQ ID NO:71:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:71:

Met Gly Ala Arg Ala Ser Val Leu Ser Gly Gly Lys Leu Asp Ala Trp
         1               5                  10                  15
```

```
    Glu Arg Ile Arg Leu Arg Pro Gly Gly Lys Lys Thr Tyr Arg Leu Lys
                    20                  25                  30

His Leu Val Trp Ala Ser Arg Glu Leu Glu Arg Phe Ala Leu His Pro
                    35                  40                  45

Gly Leu Leu Glu Thr Ala Glu Gly Cys Gln Gln Leu Met Asp Gln Leu
                50                  55                  60

Gln Ser Ala Leu Arg Thr Gly Ser Glu Glu Leu Ile Ser Leu Tyr Asn
    65                  70                  75                  80

Thr Leu Ala Thr Leu Trp Cys Val His Gln Thr Ile Glu Ile Lys Asp
                    85                  90                  95

Thr Lys Glu Ala Leu Asp Lys Ile Glu Ile Gln Ser Lys Ser Lys
                    100                 105                 110

Gln Lys Ala Gln Gln Ala Val Ala Ala Thr Gly Asn Ser Ser Asn Leu
                    115                 120                 125

Ser Gln Asn Tyr
            130

(2) INFORMATION FOR SEQ ID NO:72:

(i) SEQUENCE CHARACTERISTICS:
        (A) LENGTH: 133 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:72:

Met Gly Ala Arg Ala Ser Val Leu Ser Gly Gly Glu Leu Asp Arg Trp
    1               5                   10                  15

Glu Lys Ile Arg Leu Arg Pro Gly Gly Lys Lys Tyr Arg Leu Lys
                    20                  25                  30

His Ile Val Trp Ala Ser Arg Glu Leu Glu Arg Phe Ala Ile Asn Pro
                    35                  40                  45

Gly Leu Leu Glu Ser Ala Glu Gly Cys Gln Gln Ile Ile Glu Gln Leu
                50                  55                  60

Gln Ser Thr Leu Lys Thr Gly Ser Glu Glu Leu Lys Ser Leu Phe Asn
    65                  70                  75                  80

Thr Ile Ala Thr Leu Tyr Cys Val His Gln Arg Ile Asp Val Lys Asp
                    85                  90                  95

Thr Lys Glu Ala Leu Asp Lys Ile Glu Glu Val Gln Lys Lys Ser Lys
                    100                 105                 110

Gln Lys Thr Gln Gln Ala Ala Ala Asp Thr Gly Ser Ser Ser Lys
                    115                 120                 125

Val Ser Gln Asn Tyr
            130

(2) INFORMATION FOR SEQ ID NO:73:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:73:

Met Gly Ala Arg Ala Ser Val Leu Ser Gly Gly Lys Leu Asp Ser Trp
    1               5                   10                  15
```

```
        Glu Lys Ile Arg Leu Arg Pro Gly Gly Lys Lys Tyr Arg Met Lys
                     20                  25                  30

His Leu Val Trp Ala Ser Arg Glu Leu Glu Arg Phe Ala Val Asn Pro
                         35                  40                  45

Gly Leu Leu Glu Ser Ala Glu Gly Cys Gln Gln Ile Ile Glu Gln Leu
            50                  55                  60

Gln Pro Ala Leu Gln Thr Gly Ser Glu Glu Leu Lys Ser Leu Phe Asn
        65                  70                  75                  80

Thr Ile Ala Thr Leu Trp Cys Val His Gln Arg Ile Asp Val Lys Asp
                        85                  90                  95

Thr Lys Glu Ala Leu Asp Lys Ile Glu Glu Val Gln Arg Lys Ser Lys
                        100                 105                 110

Gln Lys Thr Gln Gln Ala Ala Asp Thr Gly Ser Ser Ser Lys Val
                        115                 120                 125

Ser Gln Asn Tyr
                130
```

(2) INFORMATION FOR SEQ ID NO:74:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:74:

```
        Met Gly Ala Arg Ala Ser Val Leu Ser Gly Gly Glu Leu Asp Arg Trp
        1               5                   10                  15

Glu Lys Ile Arg Leu Arg Pro Gly Gly Lys Lys Tyr Lys Leu Lys
                        20                  25                  30

His Ile Val Trp Ala Ser Arg Glu Leu Glu Arg Phe Ala Val Asn Pro
                        35                  40                  45

Gly Leu Leu Glu Thr Ser Glu Gly Cys Arg Gln Ile Leu Glu Gln Leu
            50                  55                  60

Gln Pro Ala Leu Gln Thr Gly Ser Glu Glu Phe Arg Ser Leu Phe Asn
        65                  70                  75                  80

Thr Val Ala Thr Leu Tyr Cys Val His Arg Arg Ile Glu Val Lys Asp
                        85                  90                  95

Thr Lys Glu Ala Leu Glu Lys Met Glu Glu Gln Asn Lys Ser Lys
                        100                 105                 110

Lys Lys Ala Gln Gln Ala Ala Ala Gly Thr Gly Asn Ser Ser Gln Val
                        115                 120                 125

Ser Gln Asn Tyr
                130
```

(2) INFORMATION FOR SEQ ID NO:75:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:75:

```
        Met Gly Ala Arg Ala Ser Val Ile Ser Gly Gly Glu Leu Asp Arg Trp
        1               5                   10                  15
```

```
        Glu Lys Ile Arg Leu Arg Pro Gly Gly His Lys Lys Tyr Arg Leu Lys
                     20                  25                  30

His Ile Val Trp Ala Ser Arg Glu Leu Glu Arg Phe Ala Val Asn Pro
                         35                  40                  45

Gly Leu Leu Glu Thr Ser Glu Gly Cys Arg Gln Ile Leu Gly Gln Leu
                     50                  55                  60

Gln Pro Ala Leu Gln Thr Gly Ser Glu Glu Leu Arg Ser Leu Tyr Asn
        65                  70                  75                  80

Thr Val Ala Thr Leu Tyr Cys Val His Gln Lys Ile Glu Val Lys Asp
                         85                  90                  95

Thr Lys Glu Ala Leu Glu Lys Ile Glu Glu Gln Asn Lys Ser Lys
                        100                 105                 110

Lys Lys Ala Gln Gln Ala Ala Ala Gly Thr Gly Asn Ser Ser Gln Val
                        115                 120                 125

Ser Gln Asn Tyr
                    130
```

(2) INFORMATION FOR SEQ ID NO:76:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:76:

```
        Met Gly Ala Arg Ala Ser Val Leu Ser Gly Gly Glu Leu Asp Arg Trp
        1                5                  10                  15

Glu Lys Ile Arg Leu Arg Pro Gly Gly Lys Lys Tyr Lys Leu Lys
                     20                  25                  30

His Ile Val Trp Ala Ser Arg Glu Leu Glu Arg Phe Ala Val Asn Pro
                         35                  40                  45

Gly Leu Leu Glu Thr Ser Glu Gly Cys Arg Gln Ile Leu Gly Gln Leu
                     50                  55                  60

Gln Pro Ser Leu Gln Thr Gly Ser Glu Glu Leu Lys Ser Leu Phe Asn
        65                  70                  75                  80

Thr Val Ala Thr Leu Tyr Cys Val His Gln Lys Ile Glu Val Xaa Asp
                         85                  90                  95

Thr Lys Glu Ala Leu Glu Lys Met Glu Glu Gln Asn Lys Ser Lys
                        100                 105                 110

Lys Xaa Ala Gln Gln Ala Ala Ala Gly Thr Gly Asn Ser Ser Gln Ile
                        115                 120                 125

Ser Gln Asn Tyr
                    130
```

(2) INFORMATION FOR SEQ ID NO:77:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:77:

```
        Met Gly Ala Arg Ala Ser Ile Leu Ser Gly Gly Glu Leu Asp Arg Trp
        1                5                  10                  15
```

```
           Glu Lys Ile Arg Leu Arg Pro Gly Gly Lys Lys Tyr Arg Leu Lys
                        20                  25                  30

His Ile Val Trp Ala Ser Arg Glu Leu Glu Arg Phe Ala Val Asn Pro
                            35                  40                  45

Gly Leu Leu Glu Thr Ser Glu Gly Cys Arg Gln Ile Leu Gly Gln Leu
                        50                  55                  60

Gln Pro Ser Leu Gln Thr Gly Ser Glu Glu Leu Arg Ser Leu Tyr Asn
           65                  70                  75                  80

Thr Val Ala Thr Leu Tyr Cys Val His Gln Lys Ile Glu Ile Lys Asp
                            85                  90                  95

Thr Lys Glu Ala Leu Asp Lys Ile Glu Glu Gln Asn Lys Ser Lys
                           100                 105                 110

Lys Lys Ala Gln Gln Ala Ala Ala Asp Thr Gly Asn Ser Ser Xaa Val
                           115                 120                 125

Ser Gln Asn Tyr
                           130
```

(2) INFORMATION FOR SEQ ID NO:78:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:78:

```
           Met Gly Ala Arg Ala Xaa Val Leu Ser Gly Gly Glu Leu Asp Arg Trp
           1               5                   10                  15

Glu Xaa Ile Arg Leu Arg Pro Gly Gly Lys Lys Tyr Lys Leu Lys
                           20                  25                  30

His Ile Val Trp Ala Ser Arg Glu Leu Glu Arg Phe Ala Val Asn Pro
                           35                  40                  45

Gly Leu Leu Glu Thr Ser Glu Gly Cys Arg Gln Ile Leu Gly Gln Leu
                           50                  55                  60

Gln Pro Ser Leu Gln Thr Gly Ser Glu Glu Leu Lys Ser Leu Phe Asn
           65                  70                  75                  80

Thr Val Ala Thr Leu Tyr Cys Val His Gln Lys Ile Glu Val Xaa Asp
                           85                  90                  95

Thr Lys Glu Ala Leu Glu Lys Val Glu Glu Gln Asn Lys Ser Lys
                           100                 105                 110

Lys Lys Ala Gln Gln Ala Ala Ala Gly Thr Gly Asn Ser Ser Gln Val
                           115                 120                 125

Ser Gln Asn Tyr
                           130
```

(2) INFORMATION FOR SEQ ID NO:79:

(i) SEQUENCE CHARACTERISTICS:
        (A) LENGTH: 135 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:79:

```
           Met Gly Ala Arg Ala Ser Val Ile Ser Gly Gly Glu Leu Asp Arg Trp
           1               5                   10                  15
```

```
      Glu Lys Ile Arg Leu Arg Pro Gly Gly His Lys Lys Tyr Arg Leu Lys
                       20                  25                  30

His Ile Val Trp Ala Ser Arg Glu Leu Glu Arg Phe Ala Val Asn Pro
                       35                  40                  45

Gly Leu Leu Glu Thr Ala Glu Gly Cys Lys Gln Ile Leu Gly Gln Leu
                       50                  55                  60

Gln Pro Ala Leu Gln Thr Gly Ser Glu Leu Arg Ser Leu Phe Asn
      65                   70                  75                  80

Thr Val Ala Val Leu Tyr Cys Val His Gln Lys Ile Asp Val Lys Asp
                           85                  90                  95

Thr Lys Glu Ala Leu Asp Lys Ile Glu Glu Gln Asn Lys Ser Lys
                          100                 105                 110

Lys Lys Ala Gln Gln Ala Ala Ala Asp Thr Gly Asn Ser Ser Asn Ser
                          115                 120                 125

Ser Gln Val Ser Gln Asn Tyr
                          130                 135
```

(2) INFORMATION FOR SEQ ID NO:80:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:80:

```
      Met Gly Ala Arg Ala Ser Val Leu Ser Gly Gly Glu Leu Asp Arg Trp
      1               5                   10                  15

Glu Lys Ile Arg Leu Arg Pro Gly Gly Lys Lys Tyr Lys Leu Lys
                       20                  25                  30

His Ile Val Trp Ala Ser Arg Glu Leu Glu Arg Phe Ala Val Asn Pro
                       35                  40                  45

Gly Leu Leu Glu Thr Ser Glu Gly Cys Arg Gln Ile Leu Gly Gln Leu
                       50                  55                  60

Gln Pro Ser Leu Gln Thr Gly Ser Glu Glu Leu Lys Ser Leu Phe Asn
      65                   70                  75                  80

Thr Val Ala Thr Leu Tyr Cys Val His Gln Lys Ile Glu Val Lys Asp
                           85                  90                  95

Thr Lys Glu Ala Leu Glu Lys Val Glu Glu Gln Asn Lys Ser Lys
                          100                 105                 110

Lys Lys Ala Gln Gln Ala Ala Ala Gly Thr Gly Asn Ser Ser Gln Val
                          115                 120                 125

Ser Gln Asn Tyr
                          130
```

(2) INFORMATION FOR SEQ ID NO:81:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:81:

```
      Met Gly Ala Arg Ala Ser Val Leu Ser Gly Gly Glu Leu Asp Arg Trp
      1               5                   10                  15
```

```
        Glu Lys Ile Arg Leu Arg Pro Gly Gly Lys Lys Tyr Arg Leu Lys
                        20                  25                  30

His Ile Val Trp Ala Ser Arg Glu Leu Glu Arg Phe Ala Val Asn Pro
                        35                  40                  45

Gly Leu Leu Glu Thr Ser Glu Gly Cys Arg Gln Ile Leu Gly Gln Leu
                        50                  55                  60

Gln Pro Ser Leu Gln Thr Gly Ser Glu Glu Leu Lys Ser Leu Phe Asn
        65                  70                  75                  80

Thr Ile Ala Thr Leu Tyr Cys Val His Gln Arg Ile Asp Val Lys Asp
                        85                  90                  95

Thr Lys Glu Ala Leu Glu Lys Ile Glu Glu Gln Asn Lys Ser Lys
                        100                 105                 110

Lys Lys Ala Gln Gln Ala Ala Thr Asp Thr Gly Asn Ser Ser Gln Val
                        115                 120                 125

Ser Gln Asn Tyr
                        130

(2) INFORMATION FOR SEQ ID NO:82:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:82:

Met Gly Ala Arg Ala Ser Val Leu Ser Gly Gly Glu Leu Asp Lys Trp
        1               5                   10                  15

Glu Arg Ile Arg Leu Arg Pro Gly Gly Lys Lys Tyr Lys Leu Lys
                        20                  25                  30

His Ile Val Trp Ala Ser Arg Glu Leu Glu Arg Phe Ala Val Asn Pro
                        35                  40                  45

Gly Leu Leu Glu Thr Thr Glu Gly Cys Lys Gln Ile Leu Glu Gln Leu
                        50                  55                  60

Gln Pro Ser Leu Gln Thr Gly Ser Glu Glu Leu Lys Ser Leu Phe Asn
        65                  70                  75                  80

Pro Val Ala Thr Leu Tyr Cys Val His Lys Arg Ile Glu Val Lys Asp
                        85                  90                  95

Pro Lys Glu Ala Leu Glu Lys Val Glu Glu Gln Thr Lys Ser Lys
                        100                 105                 110

Arg Lys Ala Gln Gln Ala Ala Ala Asp Thr Gly Asn Asn Lys Gln Val
                        115                 120                 125

Ser Gln Asn Tyr
                        130

(2) INFORMATION FOR SEQ ID NO:83:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:83:

Met Gly Ala Arg Ala Ser Val Leu Ser Gly Gly Glu Leu Asp Lys Trp
        1               5                   10                  15
```

```
        Glu Lys Ile Arg Leu Arg Pro Gly Gly Lys Lys Tyr Lys Leu Lys
                     20                  25                  30

His Ile Val Trp Ala Ser Arg Glu Leu Glu Arg Phe Ala Val Asn Pro
                         35                  40                  45

Gly Leu Leu Glu Thr Ser Gly Cys Arg Gln Ile Leu Gly Gln Leu
                     50                  55                  60

Gln Pro Ser Leu Gln Thr Gly Ser Glu Glu Leu Lys Ser Leu Tyr Asn
         65                  70                  75                  80

Thr Val Ala Thr Leu Tyr Cys Val His Gln Lys Ile Glu Val Lys Asp
                         85                  90                  95

Thr Lys Glu Ala Leu Glu Lys Ile Glu Glu Gln Asn Lys Ser Glu
                        100                 105                 110

Lys Lys Ala Gln Gln Ala Ala Ala Asp Thr Gly Asn Ser Gly Gln Val
                        115                 120                 125

Ser Gln Asn Tyr
                        130
```

(2) INFORMATION FOR SEQ ID NO:84:

(i) SEQUENCE CHARACTERISTICS:
        (A) LENGTH: 138 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:84:

```
        Met Gly Ala Arg Ala Ser Val Leu Ser Gly Gly Glu Leu Asp Arg Trp
         1               5                  10                  15

Glu Asn Ile Arg Leu Arg Pro Gly Gly Lys Lys Tyr Lys Leu Lys
                     20                  25                  30

His Ile Val Trp Ala Ser Arg Glu Leu Glu Arg Phe Ala Val Asn Pro
                         35                  40                  45

Gly Leu Leu Glu Thr Ser Gly Cys Arg Gln Ile Leu Glu Gln Leu
                     50                  55                  60

Gln Pro Ser Leu Gln Thr Gly Ser Glu Glu Leu Lys Ser Leu Phe Asn
         65                  70                  75                  80

Thr Val Ala Thr Leu Tyr Cys Val His Gln Lys Ile Asp Val Lys Asp
                         85                  90                  95

Xaa Thr Lys Glu Ala Leu Asp Lys Ile Glu Glu Glu Gln Thr Lys Ser
                        100                 105                 110

Lys Lys Lys Ala Gln Gln Ala Ala Ala Gly Thr Gly Asn Leu Ala Thr
                        115                 120                 125

Gly Asn Xaa Ser Gln Val Ser Gln Asn Tyr
                        130                 135
```

(2) INFORMATION FOR SEQ ID NO:85:

(i) SEQUENCE CHARACTERISTICS:
        (A) LENGTH: 135 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:85:

```
        Met Gly Ala Arg Xaa Ser Val Leu Ser Gly Gly Glu Leu Asp Arg Trp
         1               5                  10                  15
```

```
       Glu Lys Ile Arg Leu Arg Pro Gly Gly Lys Lys Tyr Arg Leu Lys
                    20                  25                  30

His Ile Val Trp Ala Xaa Arg Xaa Leu Glu Arg Phe Ala Val Asn Pro
                        35                  40                  45

Gly Leu Leu Glu Thr Ser Glu Gly Cys Arg Gln Ile Leu Glu Gln Leu
                    50                  55                  60

Gln Pro Ser Leu Gln Xaa Gly Ser Glu Glu Leu Arg Ser Leu Phe Asn
        65                  70                  75                  80

Pro Ile Ala Thr Leu Tyr Cys Val His Gln Arg Ile Asp Val Xaa Pro
                        85                  90                  95

Thr Lys Glu Ala Leu Glu Lys Ile Glu Glu Gln Thr Lys Ser Lys
                       100                 105                 110

Lys Lys Ala Gln Gln Ala Gln Ala Ala Gly Thr Gly Asn Ser
                       115                 120                 125

Ser Gln Val Ser Gln Asn Tyr
                       130                 135
```

(2) INFORMATION FOR SEQ ID NO:86:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:86:

```
       Met Gly Ala Arg Ala Ser Val Leu Ser Gly Gly Glu Leu Asp Arg Trp
        1               5                  10                  15

Glu Lys Ile Arg Leu Arg Pro Gly Gly Lys Lys Tyr Lys Leu Lys
                    20                  25                  30

His Ile Val Trp Ala Ser Arg Glu Leu Glu Arg Phe Ala Val Asn Pro
                        35                  40                  45

Gly Leu Leu Glu Thr Ser Gly Gly Cys Arg Gln Ile Leu Glu Gln Leu
                    50                  55                  60

Gln Pro Ser Leu Gln Thr Gly Ser Glu Glu Leu Lys Ser Leu Tyr Asn
        65                  70                  75                  80

Ala Val Ala Val Leu Tyr Cys Val His Gln Lys Ile Asp Val Lys Asp
                        85                  90                  95

Thr Lys Glu Ala Leu Glu Lys Ile Glu Glu Gln Asn Lys Ser Lys
                       100                 105                 110

Lys Lys Ala Gln Gln Ala Ala Ala Gly Thr Gly Asn Ser Ser Gln Val
                       115                 120                 125

Ser Gln Asn Tyr
                       130
```

(2) INFORMATION FOR SEQ ID NO:87:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:87:

```
       Met Gly Ala Arg Ala Ser Val Ile Ser Gly Gly Glu Leu Asp Arg Trp
        1               5                  10                  15
```

```
    Glu Lys Ile Arg Leu Arg Pro Gly Gly Ser Lys Lys Tyr Arg Leu Lys
                 20                  25                  30

His Ile Val Trp Ala Ser Arg Glu Leu Glu Arg Phe Ala Val Asn Pro
                 35                  40                  45

Gly Leu Leu Glu Thr Ser Glu Gly Cys Arg Gln Ile Leu Arg Gln Leu
                 50                  55                  60

Gln Pro Ser Leu Gln Thr Gly Ser Glu Glu Leu Arg Ser Leu Tyr Asn
     65                  70                  75                  80

Thr Val Ala Thr Leu Tyr Cys Val His Gln Lys Ile Glu Val Lys Asp
                         85                  90                  95

Thr Lys Glu Ala Leu Glu Lys Val Glu Glu Gln Asn Lys Ser Lys
                        100                 105                 110

Lys Lys Ala Gln Gln Ala Ala Ala Asp Thr Gly Asn Ser Ser Gln Val
                        115                 120                 125

Ser Gln Asn Tyr
                130

(2) INFORMATION FOR SEQ ID NO:88:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:88:

Met Gly Ala Arg Ala Ser Val Leu Ser Gly Gly Glu Leu Asp Arg Trp
     1                   5                  10                  15

Glu Lys Ile Arg Leu Arg Pro Gly Gly Lys Lys Tyr Arg Leu Lys
                 20                  25                  30

His Ile Val Trp Ala Ser Arg Glu Leu Glu Arg Phe Ala Val Asn Pro
                 35                  40                  45

Gly Leu Leu Glu Thr Ser Glu Gly Cys Arg Gln Ile Leu Gly Gln Leu
                 50                  55                  60

Gln Pro Ser Leu Gln Thr Gly Ser Glu Glu Leu Arg Ser Leu Phe Asn
     65                  70                  75                  80

Thr Val Ala Thr Leu Tyr Cys Val His Gln Lys Ile Asp Val Lys Asp
                         85                  90                  95

Thr Lys Glu Ala Leu Glu Lys Val Glu Glu Gln Asn Lys Ser Lys
                        100                 105                 110

Lys Lys Ala Gln Gln Ala Ala Ala Gly Thr Gly Asn Ser Ser Gln Val
                        115                 120                 125

Ser Gln Asn Tyr
                130

(2) INFORMATION FOR SEQ ID NO:89:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:89:

Met Gly Ala Arg Ala Ser Val Leu Ser Gly Gly Glu Leu Asp Arg Trp
     1                   5                  10                  15
```

```
        Glu Lys Ile Arg Leu Arg Pro Gly Gly Lys Lys Tyr Arg Leu Lys
                     20                  25                  30

His Ile Val Trp Ala Ser Arg Glu Leu Glu Arg Phe Ala Val Asn Pro
                         35                  40                  45

Gly Leu Leu Glu Ser Ser Glu Gly Cys Arg Gln Ile Leu Gly Gln Leu
                     50                  55                  60

Gln Pro Ser Leu Gln Thr Gly Ser Glu Glu Leu Arg Ser Leu Tyr Asn
        65                  70                  75                  80

Thr Ile Ala Thr Leu Tyr Cys Val His Gln Lys Ile Glu Val Lys Asp
                         85                  90                  95

Thr Lys Glu Ala Leu Glu Lys Ile Glu Glu Gln Asn Lys Ser Lys
                        100                 105                 110

Lys Lys Ala Gln Gln Ala Ala Ala Gly Thr Gly Asn Ser Ser Gln Val
                        115                 120                 125

Ser Gln Asn Tyr
                    130

(2) INFORMATION FOR SEQ ID NO:90:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:90:

Met Gly Ala Arg Ala Ser Val Leu Ser Gly Gly Glu Leu Asp Arg Trp
        1               5                   10                  15

Glu Lys Ile Arg Leu Arg Pro Gly Gly Lys Lys Tyr Lys Leu Lys
                     20                  25                  30

His Ile Val Trp Ala Ser Arg Glu Leu Glu Arg Phe Ala Val Asn Pro
                         35                  40                  45

Gly Leu Leu Glu Thr Ser Glu Gly Cys Arg Gln Ile Leu Gly Gln Leu
                     50                  55                  60

Gln Pro Ala Leu Gln Thr Gly Ser Glu Glu Leu Lys Ser Leu Phe Asn
        65                  70                  75                  80

Ala Val Ala Val Leu Tyr Cys Val His Gln Lys Ile Asp Ile Lys Asp
                         85                  90                  95

Thr Lys Glu Ala Leu Glu Lys Ile Glu Glu Gln Asn Lys Ser Lys
                        100                 105                 110

Lys Lys Ala Gln Gln Ala Ala Ala Gly Thr Gly Asn Ser Ser Gln Val
                        115                 120                 125

Ser Gln Asn Tyr
                    130

(2) INFORMATION FOR SEQ ID NO:91:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:91:

Met Gly Ala Arg Ala Ser Val Leu Ser Gly Gly Glu Leu Asp Arg Trp
        1               5                   10                  15
```

Glu Lys Ile Arg Leu Arg Pro Gly Gly Lys Lys Arg Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
        50                  55                  60

Gln Pro Ser Leu Gln Thr Gly Ser Glu Glu Leu Lys Ser Leu Phe Asn
65                  70                  75                  80

Thr Val Ala Thr Leu Tyr Cys Val His Gln Lys Ile Glu Val Lys Asp
                85                  90                  95

Thr Lys Glu Ala Leu Asp Lys Ile Glu Glu Gln Asn Lys Ser Lys
                100                 105                 110

Lys Lys Ala Gln Gln Ala Ala Ala Asp Thr Arg Ser Ser Ser Gln Val
                115                 120                 125

Ser Gln Asn Tyr
        130

(2) INFORMATION FOR SEQ ID NO:92:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:92:

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Arg Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
        50                  55                  60

Gln Pro Ser Leu Gln Thr Gly Ser Glu Glu Leu Lys Ser Leu Phe Asn
65                  70                  75                  80

Thr Val Ala Thr Leu Tyr Cys Val His Gln Lys Ile Glu Val Lys Asp
                85                  90                  95

Thr Lys Glu Ala Leu Asp Lys Ile Glu Glu Gln Asn Lys Ser Lys
                100                 105                 110

Lys Lys Ala Gln Gln Ala Ala Ala Asp Thr Arg Ser Ser Ser Gln Val
                115                 120                 125

Ser Gln Asn Tyr
        130

(2) INFORMATION FOR SEQ ID NO:93:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:93:

Met Gly Ala Arg Ala Ser Val Leu Ser Gly Gly Lys Leu Asp Ser Trp
1               5                   10                  15

```
        Glu Lys Ile Arg Leu Arg Pro Gly Gly Lys Lys Tyr Arg Leu Lys
                     20                  25                  30

His Ile Val Trp Ala Ser Arg Glu Leu Glu Arg Phe Ala Val Asn Pro
                         35                  40                  45

Gly Leu Leu Glu Thr Ser Glu Gly Cys Arg Gln Ile Leu Gly Gln Leu
             50                  55                  60

Gln Pro Ala Leu Gln Thr Gly Ser Glu Glu Leu Arg Ser Leu Tyr Asn
        65                  70                  75                  80

Thr Val Ala Thr Leu Tyr Cys Val His Gln Arg Ile Asp Val Lys Asp
                         85                  90                  95

Thr Lys Glu Ala Leu Asp Lys Ile Glu Glu Gln Asn Lys Ser Lys
                        100                 105                 110

Lys Lys Ala Gln Gln Ala Ala Ala Asp Thr Gly Asn Ser Ser Lys Val
                        115                 120                 125

Ser Gln Asn Tyr
                130
```

(2) INFORMATION FOR SEQ ID NO:94:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:94:

```
        Met Gly Ala Arg Ala Ser Val Leu Ser Gly Gly Lys Leu Asp Ser Trp
        1               5                  10                  15

Glu Lys Ile Arg Leu Arg Pro Gly Gly Lys Lys Tyr Arg Leu Lys
                     20                  25                  30

His Ile Val Trp Ala Ser Arg Glu Leu Glu Arg Phe Ala Val Asn Pro
                         35                  40                  45

Gly Leu Leu Glu Thr Ser Glu Gly Cys Arg Gln Ile Leu Gly Gln Leu
             50                  55                  60

Gln Pro Ala Leu Gln Thr Gly Ser Glu Glu Leu Arg Ser Leu Tyr Asn
        65                  70                  75                  80

Thr Val Ala Thr Leu Tyr Cys Val His Gln Arg Ile Asp Val Lys Asp
                         85                  90                  95

Thr Lys Glu Ala Leu Asp Lys Ile Glu Glu Gln Asn Lys Ser Lys
                        100                 105                 110

Lys Lys Ala Gln Gln Ala Ala Ala Asp Thr Gly Asn Ser Gly Pro Val
                        115                 120                 125

Ser Gln Asn Tyr
                130
```

(2) INFORMATION FOR SEQ ID NO:95:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:95:

```
        Met Gly Ala Arg Ala Ser Val Leu Ser Gly Gly Glu Leu Asp Arg Trp
        1               5                  10                  15
```

```
          Glu Lys Ile Arg Leu Arg Pro Gly Gly Lys Lys Gln Tyr Lys Leu Lys
                       20                  25                  30

His Ile Val Trp Ala Ser Arg Glu Leu Glu Arg Phe Ala Val Asn Pro
                       35                  40                  45

Gly Leu Leu Glu Thr Ser Glu Gly Cys Arg Gln Ile Leu Gly Gln Leu
                       50                  55                  60

Gln Pro Ser Leu Gln Thr Gly Ser Glu Glu Leu Gln Ser Leu Phe Asn
           65                  70                  75                  80

Thr Ile Ala Thr Leu Tyr Cys Val His Gln Arg Ile Asp Val Lys Asp
                           85                  90                  95

Thr Lys Glu Ala Leu Glu Lys Ile Glu Glu Gln Asn Lys Ser Lys
                          100                 105                 110

Lys Lys Ala Gln Gln Thr Ala Ala Gly Thr Gly Asn Ser Ser Gln Val
                          115                 120                 125

Ala Gln Asn Tyr
                  130

(2) INFORMATION FOR SEQ ID NO:96:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:96:

Met Gly Ala Arg Ala Ser Val Leu Ser Gly Gly Glu Leu Asp Arg Trp
         1               5                  10                  15

Glu Lys Ile Arg Leu Arg Pro Gly Gly Lys Lys Gln Tyr Lys Leu Lys
                     20                  25                  30

His Ile Val Trp Ala Ser Arg Glu Leu Glu Arg Phe Ala Val Asn Pro
                     35                  40                  45

Gly Leu Leu Glu Thr Ser Glu Gly Cys Arg Gln Ile Leu Gly Gln Leu
                     50                  55                  60

Gln Pro Ser Leu Gln Thr Gly Ser Glu Glu Leu Lys Ser Leu Phe Asn
         65                  70                  75                  80

Thr Ile Ala Thr Leu Tyr Cys Val His Gln Arg Ile Asp Val Lys Asp
                         85                  90                  95

Thr Lys Glu Ala Leu Glu Lys Ile Glu Glu Gln Asn Lys Ser Lys
                        100                 105                 110

Lys Lys Ala Gln Gln Ala Ala Ala Gly Thr Gly Asn Ser Ser Gln Val
                        115                 120                 125

Ala Gln Asn Tyr
                130

(2) INFORMATION FOR SEQ ID NO:97:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:97:

Met Gly Ala Arg Ala Ser Val Leu Ser Gly Gly Glu Leu Asp Arg Trp
         1               5                  10                  15
```

```
Glu Lys Ile Arg Leu Arg Pro Gly Gly Lys Lys Tyr Arg Leu Lys
             20                  25                  30

His Ile Val Trp Ala Ser Arg Glu Leu Glu Arg Phe Ala Val Asn Pro
             35                  40                  45

Gly Leu Leu Glu Thr Ser Glu Gly Cys Lys Gln Ile Leu Glu Gln Leu
 50                  55                  60

Gln Pro Ala Leu Gln Thr Gly Ser Glu Glu Leu Arg Ser Leu Phe Asn
 65                  70                  75                  80

Thr Val Ala Thr Leu Tyr Cys Val His Gln Lys Ile Asp Val Lys Asp
                 85                  90                  95

Thr Lys Glu Ala Leu Glu Lys Ile Glu Glu Gln Asn Lys Ser Lys
                100                 105                 110

Lys Lys Ala Gln Gln Ala Ala Ala Gly Thr Gly Asn Ser Ser Gln Ala
             115                 120                 125

Ser Gln Asn Tyr
         130
```

(2) INFORMATION FOR SEQ ID NO:98:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:98:

```
Met Gly Ala Arg Ala Ser Val Leu Ser Gly Gly Glu Leu Asp Arg Trp
 1               5                  10                  15

Glu Lys Ile Arg Leu Arg Pro Gly Gly Lys Lys Tyr Arg Leu Lys
             20                  25                  30

His Ile Val Trp Ala Ser Arg Glu Leu Glu Arg Phe Ala Val Asn Pro
             35                  40                  45

Gly Leu Leu Glu Thr Ser Glu Gly Cys Lys Gln Ile Leu Glu Gln Leu
 50                  55                  60

Gln Pro Ala Leu Gln Thr Gly Ser Glu Glu Leu Arg Ser Leu Phe Asn
 65                  70                  75                  80

Thr Val Ala Thr Leu Tyr Cys Val His Gln Lys Ile Asp Val Lys Asp
                 85                  90                  95

Thr Lys Glu Ala Leu Glu Lys Ile Glu Glu Gln Asn Lys Ser Lys
                100                 105                 110

Lys Lys Ala Gln Gln Ala Ala Ala Gly Thr Gly Asn Ser Ser Gln Ala
             115                 120                 125

Ser Gln Asn Tyr
         130
```

(2) INFORMATION FOR SEQ ID NO:99:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:99:

```
Met Gly Ala Arg Ala Ser Val Leu Ser Gly Gly Glu Leu Asp Arg Trp
 1               5                  10                  15
```

-continued

```
Glu Lys Ile Arg Leu Arg Pro Gly Gly Lys Lys Tyr Lys Leu Lys
             20                  25                  30

His Ile Val Trp Ala Ser Arg Glu Leu Glu Arg Phe Ala Val Asn Pro
             35                  40                  45

Gly Leu Leu Glu Thr Ser Glu Gly Cys Arg Gln Ile Leu Glu Gln Leu
             50                  55                  60

Gln Pro Ala Leu Gln Thr Gly Ser Glu Glu Leu Arg Ser Leu Phe Asn
 65                  70                  75                  80

Thr Val Ala Ser Leu Tyr Cys Val His Gln Arg Ile Asp Val Lys Asp
                 85                  90                  95

Ala Lys Glu Ala Leu Glu Lys Ile Glu Glu Gln Asn Lys Ser Lys
             100                 105                 110

Lys Lys Ala Gln Gln Ala Ala Ala Gly Thr Gly Asn Asn Ser Gln Val
             115                 120                 125

Ser Gln Asn Tyr
             130
```

(2) INFORMATION FOR SEQ ID NO:100:

(i) SEQUENCE CHARACTERISTICS:
        (A) LENGTH: 134 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:100:

```
Met Gly Ala Arg Ala Ser Val Leu Ser Gly Gly Glu Leu Asp Arg Trp
 1               5                  10                  15

Glu Lys Ile Arg Leu Arg Pro Gly Gly Lys Lys Tyr Lys Leu Lys
             20                  25                  30

His Ile Val Trp Ala Ser Arg Glu Leu Glu Arg Phe Ala Val Asn Pro
             35                  40                  45

Gly Leu Leu Glu Thr Ser Glu Gly Cys Arg Gln Ile Leu Glu Gln Leu
             50                  55                  60

Gln Pro Ala Leu Gln Thr Gly Ser Glu Glu Leu Arg Ser Leu Phe Asn
 65                  70                  75                  80

Thr Val Ala Thr Leu Trp Cys Val His Gln Arg Ile Asp Val Lys Asp
                 85                  90                  95

Thr Lys Glu Ala Leu Glu Lys Ile Glu Glu Gln Asn Lys Ser Lys
             100                 105                 110

Lys Lys Ala Gln Gln Ala Ala Ala Gly Thr Gly Asn Ser Ser Gln Val
             115                 120                 125

Ser Val Ser Gln Asn Tyr
             130
```

(2) INFORMATION FOR SEQ ID NO:101:

(i) SEQUENCE CHARACTERISTICS:
        (A) LENGTH: 133 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:101:

```
Met Gly Ala Arg Ala Ser Val Leu Ser Gly Gly Glu Leu Asp Arg Trp
 1               5                  10                  15
```

```
    Glu Lys Ile Arg Leu Arg Pro Gly Gly Lys Lys Tyr Arg Leu Lys
                 20                  25                  30

His Ile Val Trp Ala Ser Arg Glu Leu Glu Arg Phe Ala Leu Asn Pro
                 35                  40                  45

Gly Leu Leu Glu Ala Ser Glu Gly Cys Arg Gln Ile Leu Gly Gln Leu
                 50                  55                  60

Gln Pro Ser Leu Gln Thr Gly Ser Glu Glu Leu Xaa Ser Leu Phe Asn
     65                  70                  75                  80

Xaa Val Ala Thr Leu Tyr Cys Val His Gln Lys Ile Asp Val Lys Asp
                 85                  90                  95

Ala Lys Glu Ala Leu Asp Lys Ile Glu Glu Gln Asn Lys Ser Lys
                100                 105                 110

Lys Lys Xaa Gln Xaa Ala Ala Ala Gly Pro Gly Asn Ser Ser Gln
                115                 120                 125

Val Ser Gln Asn Tyr
    130
```

(2) INFORMATION FOR SEQ ID NO:102:

(i) SEQUENCE CHARACTERISTICS:
        (A) LENGTH: 133 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:102:

```
    Met Gly Ala Arg Ala Ser Val Leu Ser Gly Gly Glu Leu Asp Arg Trp
     1               5                  10                  15

Glu Lys Ile Arg Leu Arg Pro Gly Gly Lys Xaa Lys Tyr Arg Leu Lys
                 20                  25                  30

His Ile Val Trp Ala Ser Arg Glu Leu Glu Arg Phe Xaa Leu Asn Pro
                 35                  40                  45

Gly Leu Leu Glu Thr Ser Glu Gly Cys Arg Gln Ile Leu Gly Gln Leu
                 50                  55                  60

Gln Pro Ser Leu Gln Thr Gly Ser Glu Xaa Leu Lys Ser Leu Tyr Xaa
     65                  70                  75                  80

Thr Xaa Ala Thr Xaa Tyr Cys Val His Gln Lys Ile Asp Val Lys Asp
                 85                  90                  95

Thr Lys Glu Ala Leu Asp Lys Ile Glu Glu Gln Asn Lys Ser Lys
                100                 105                 110

Lys Lys Ala Gln Gln Ala Ala Ala Gly Pro Gly Asn Ser Ser Gln
                115                 120                 125

Val Ser Gln Asn Tyr
    130
```

(2) INFORMATION FOR SEQ ID NO:103:

(i) SEQUENCE CHARACTERISTICS:
        (A) LENGTH: 136 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:103:

```
    Met Gly Ala Arg Ala Ser Ile Leu Ser Gly Gly Leu Asp Arg Trp
     1               5                  10                  15
```

```
    Glu Lys Ile Arg Leu Arg Pro Gly Gly Lys Lys Tyr Xaa Leu Lys
                 20                  25                  30

His Ile Val Trp Ala Ser Arg Glu Leu Glu Arg Phe Ala Xaa Asn Pro
                     35                  40                  45

Gly Leu Leu Glu Thr Ser Glu Gly Cys Arg Gln Ile Leu Gly Gln Leu
                 50                  55                  60

Gln Pro Ser Leu Gln Thr Gly Ser Glu Glu Leu Arg Ser Xaa Phe Asn
    65                  70                  75                  80

Thr Val Ala Pro Leu Tyr Cys Val His Gln Lys Xaa Asp Val Lys Asp
                         85                  90                  95

Thr Lys Glu Ala Leu Asp Lys Ile Glu Glu Gln Asn Lys Ser Lys
                     100                 105                 110

Lys Lys Ala Gln Gln Ala Ala Ala Gly Thr Gly Asn Ser Xaa Gln Ala
                     115                 120                 125

Ser Asn Gln Val Ser Gln Asn Tyr
                     130                 135
```

(2) INFORMATION FOR SEQ ID NO:104:

(i) SEQUENCE CHARACTERISTICS:
        (A) LENGTH: 136 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:104:

```
    Met Gly Ala Arg Ala Ser Val Leu Ser Gly Gly Gly Leu Asp Arg Trp
    1               5                   10                  15

Glu Xaa Ile Arg Leu Arg Pro Gly Gly Lys Lys Tyr Arg Leu Lys
                     20                  25                  30

His Ile Val Trp Ala Ser Arg Glu Leu Glu Arg Phe Ala Xaa Asn Pro
                     35                  40                  45

Gly Leu Leu Glu Thr Ser Glu Gly Cys Arg Gln Ile Leu Gly Gln Leu
                 50                  55                  60

Gln Pro Ser Leu Gln Thr Gly Ser Glu Glu Leu Arg Ser Leu Phe Asn
    65                  70                  75                  80

Thr Val Ala Thr Leu Tyr Cys Val His Gln Xaa Arg Asp Val Lys Asp
                         85                  90                  95

Thr Lys Glu Ala Leu Asp Lys Ile Glu Glu Gln Asn Lys Ser Lys
                     100                 105                 110

Glu Lys Ala Gln Gln Lys Ala Gln Gln Ala Ala Thr Gly Thr Gly Asn
                     115                 120                 125

Ser Ser Gln Val Ser Gln Asn Tyr
                     130                 135
```

(2) INFORMATION FOR SEQ ID NO:105:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:105:

```
    Met Gly Ala Arg Ala Ser Val Leu Ser Gly Gly Glu Leu Asp Arg Trp
    1               5                   10                  15
```

```
    Glu Lys Ile Arg Leu Arg Pro Gly Gly Lys Lys Tyr Arg Leu Lys
                 20                  25                  30

His Ile Val Trp Ala Ser Arg Glu Leu Glu Arg Phe Ala Val Asn Pro
                     35                  40                  45

Gly Leu Leu Glu Thr Ser Gly Gly Cys Arg Gln Ile Leu Gly Gln Leu
                 50                  55                  60

Gln Pro Ser Leu Gln Thr Gly Ser Glu Glu Leu Arg Ser Leu Phe Asn
    65                  70                  75                  80

Thr Val Ala Thr Leu Tyr Cys Val His Gln Lys Ile Glu Val Lys Asp
                         85                  90                  95

Thr Lys Glu Ala Leu Glu Lys Ile Glu Glu Gln Asn Lys Ser Lys
                     100                 105                 110

Lys Lys Thr Gln Gln Ala Ala Leu Ala Thr Gly Asn Ser Gly Gln Ala
                     115                 120                 125

Ser Gln Asn Tyr
                130

(2) INFORMATION FOR SEQ ID NO:106:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:106:

Met Gly Ala Arg Ala Ser Val Leu Ser Gly Gly Glu Leu Asp Arg Trp
    1               5                   10                  15

Glu Lys Ile Arg Leu Arg Pro Gly Gly Lys Lys Tyr Arg Leu Lys
                 20                  25                  30

His Ile Val Trp Ala Ser Arg Glu Leu Glu Arg Phe Ala Val Asn Pro
                     35                  40                  45

Gly Leu Leu Glu Thr Ser Gly Gly Cys Arg Gln Ile Leu Gly Gln Leu
                 50                  55                  60

Gln Pro Ser Leu Gln Thr Gly Ser Glu Glu Leu Arg Ser Leu Phe Asn
    65                  70                  75                  80

Thr Val Ala Thr Leu Tyr Cys Val His Gln Lys Ile Glu Val Lys Asp
                         85                  90                  95

Thr Lys Glu Ala Leu Glu Lys Ile Glu Glu Gln Asn Lys Ser Lys
                     100                 105                 110

Lys Lys Thr Gln Gln Ala Ala Leu Ala Thr Gly Asn Ser Gly Gln Ala
                     115                 120                 125

Ser Gln Asn Tyr
                130

(2) INFORMATION FOR SEQ ID NO:107:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:107:

Met Gly Ala Arg Xaa Ser Val Leu Ser Gly Gly Xaa Leu Asp Lys Trp
    1               5                   10                  15
```

```
    Glu Lys Ile Arg Leu Arg Pro Gly Xaa Lys Lys Tyr Lys Leu Lys
                 20                  25                  30

His Ile Val Trp Ala Ser Arg Glu Leu Glu Arg Phe Ala Val Asn Pro
                     35                  40                  45

Gly Leu Leu Glu Thr Ser Glu Gly Cys Arg Gln Ile Leu Gly Gln Leu
            50                  55                  60

Gln Pro Xaa Leu Arg Thr Gly Ser Glu Glu Leu Lys Ser Leu Phe Asn
    65                  70                  75                  80

Ala Val Ala Val Leu Tyr Cys Val His Gln Gly Ile Glu Val Arg Asp
                    85                  90                  95

Thr Lys Glu Ala Leu Glu Lys Ile Glu Glu Gln Asn Lys Ser Lys
                    100                 105                 110

Glu Lys Ala Gln Gln Asp Thr Val Asp Thr Gly Asn Asn Ser Gln Val
                    115                 120                 125

Ser Gln Asn Tyr
            130
```

(2) INFORMATION FOR SEQ ID NO:108:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:108:

```
    Met Gly Ala Arg Ala Ser Ile Leu Ser Gly Gly Glu Leu Asp Arg Trp
    1               5                   10                  15

Glu Lys Ile Arg Leu Arg Pro Gly Gly Lys Lys Tyr Arg Leu Lys
                 20                  25                  30

His Ile Val Trp Ala Ser Arg Glu Leu Glu Arg Phe Ala Val Asn Pro
                     35                  40                  45

Gly Leu Leu Glu Thr Ser Gly Gly Cys Arg Gln Ile Leu Glu Gln Leu
            50                  55                  60

Gln Pro Ser Leu Gln Thr Gly Ser Glu Glu Leu Arg Ser Leu Tyr Asn
    65                  70                  75                  80

Thr Val Ala Thr Leu Tyr Cys Val His Gln Lys Ile Asp Val Lys Asp
                    85                  90                  95

Thr Lys Glu Ala Leu Glu Lys Ile Glu Glu Gln Asn Lys Ser Lys
                    100                 105                 110

Lys Lys Glu Gln Gln Ala Ala Ala Gly Thr Gly Asn Ser Ser Gln Val
                    115                 120                 125

Ser Gln Asn Tyr
            130
```

(2) INFORMATION FOR SEQ ID NO:109:

(i) SEQUENCE CHARACTERISTICS:
        (A) LENGTH: 135 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:109:

```
    Met Gly Ala Arg Ala Ser Val Leu Ser Gly Gly Glu Leu Asp Arg Trp
    1               5                   10                  15
```

```
        Glu Lys Ile Arg Leu Arg Pro Gly Gly Lys Lys Arg Tyr Lys Leu Lys
                    20                  25                  30

His Ile Val Trp Ala Ser Arg Glu Leu Glu Arg Phe Ala Val Asn Pro
                    35                  40                  45

Gly Leu Leu Glu Thr Ser Glu Gly Cys Arg Gln Ile Leu Gly Gln Leu
                    50                  55                  60

Gln Pro Ser Leu Gln Thr Gly Ser Glu Glu Leu Arg Ser Leu Tyr Asn
        65                  70                  75                  80

Thr Val Ala Thr Leu Tyr Cys Val His Gln Lys Ile Asp Val Lys Asp
                            85                  90                  95

Thr Lys Glu Ala Leu Glu Lys Ile Glu Glu Gln Asn Lys Ser Lys
                        100                 105                 110

Lys Lys Ala Gln Gln Ala Ala Gly Thr Gly Asn Ser Ser Gln Val
                        115                 120                 125

Ile Gln Ala Ser Gln Asn Phe
                        130             135
```

(2) INFORMATION FOR SEQ ID NO:110:

(i) SEQUENCE CHARACTERISTICS:
        (A) LENGTH: 133 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:110:

```
        Met Gly Ala Arg Ala Ser Val Leu Ser Gly Gly Lys Leu Asp Arg Trp
        1               5                   10                  15

Glu Lys Ile Arg Leu Arg Pro Gly Gly Lys Lys Tyr Lys Leu Lys
                    20                  25                  30

His Ile Val Trp Ala Ser Arg Glu Leu Glu Arg Phe Ala Val Asn Pro
                    35                  40                  45

Gly Leu Leu Glu Thr Ala Glu Gly Cys Arg Gln Ile Leu Gly Gln Leu
                    50                  55                  60

Gln Pro Ser Leu Gln Thr Gly Ser Glu Glu Leu Lys Ser Leu Phe Asn
        65                  70                  75                  80

Thr Val Ala Thr Leu Tyr Cys Val His Gln Gly Ile Asp Val Lys Asp
                            85                  90                  95

Thr Lys Glu Ala Leu Glu Lys Ile Glu Glu Gln Asn Lys Ser Lys
                        100                 105                 110

Lys Gln Ala Gln Gln Thr Ala Ala Gly Thr Gly Asn Ser Ser Gln
                        115                 120                 125

Val Ser His Asn Tyr
                130
```

(2) INFORMATION FOR SEQ ID NO:111:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:111:

```
        Met Gly Ala Arg Ala Ser Val Leu Ser Gly Gly Glu Leu Asp Arg Trp
        1               5                   10                  15
```

-continued

```
         Glu  Lys  Ile  Arg  Leu  Arg  Pro  Gly  Gly  Lys  Lys  Tyr  Arg  Leu  Lys
                        20                       25                       30

His  Ile  Val  Trp  Ala  Ser  Arg  Glu  Leu  Glu  Arg  Phe  Ala  Val  Asn  Pro
                        35                       40                       45

Gly  Leu  Leu  Glu  Thr  Ser  Glu  Gly  Cys  Arg  Gln  Ile  Leu  Gly  Gln  Leu
                        50                       55                       60

Gln  Pro  Ser  Leu  Gln  Thr  Gly  Ser  Glu  Glu  Leu  Arg  Ser  Leu  Tyr  Asn
         65                       70                       75                        80

Thr  Val  Ala  Thr  Leu  Tyr  Cys  Val  His  Gln  Lys  Ile  Asp  Val  Lys  Asp
                             85                       90                       95

Thr  Lys  Glu  Ala  Leu  Asp  Lys  Ile  Glu  Glu  Gln  Asn  Lys  Ser  Lys
                             100                      105                      110

Lys  Lys  Ala  Gln  Gln  Ala  Ala  Ala  Asp  Thr  Gly  Asn  Ser  Ser  Gln  Val
                             115                      120                      125

Ser  Gln  Asn  Tyr
                             130
```

(2) INFORMATION FOR SEQ ID NO:112:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:112:

```
         Met  Gly  Ala  Arg  Ala  Ser  Val  Leu  Ser  Gly  Gly  Lys  Leu  Asp  Ala  Phe
         1                        5                        10                       15

Glu  Lys  Ile  Arg  Leu  Arg  Pro  Gly  Gly  Lys  Lys  Tyr  Lys  Leu  Lys
                        20                       25                       30

His  Ile  Val  Trp  Ala  Ser  Arg  Glu  Leu  Glu  Arg  Phe  Ala  Leu  Asn  Pro
                        35                       40                       45

Gly  Leu  Leu  Glu  Thr  Ala  Glu  Gly  Cys  Gln  Gln  Ile  Ile  Arg  Gln  Leu
                        50                       55                       60

Gln  Pro  Ser  Leu  Gln  Thr  Gly  Thr  Glu  Glu  Leu  Lys  Ser  Leu  Tyr  Asn
         65                       70                       75                        80

Thr  Val  Val  Thr  Leu  Tyr  Cys  Val  His  Gln  Lys  Ile  Asp  Val  Arg  Asp
                             85                       90                       95

Thr  Lys  Glu  Ala  Leu  Glu  Glu  Val  Glu  Lys  Arg  Gln  Lys  Ile  Ser  Gln
                             100                      105                      110

Gln  Lys  Ile  Gln  Gln  Ala  Ala  Xaa  Asp  Lys  Glu  Asn  Ser  Arg  Gln  Val
                             115                      120                      125

Ser  Gln  Asn  Tyr
                             130
```

(2) INFORMATION FOR SEQ ID NO:113:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:113:

```
         Met  Gly  Ala  Arg  Ala  Ser  Val  Leu  Ser  Gly  Gly  Lys  Leu  Asp  Ala  Phe
         1                        5                        10                       15
```

```
        Glu Lys Ile Arg Leu Arg Pro Gly Gly Lys Lys Tyr Lys Leu Lys
                     20                  25                  30

His Ile Val Trp Ala Ser Arg Glu Leu Glu Arg Phe Ala Leu Asn Pro
                         35                  40                  45

Gly Leu Leu Glu Thr Thr Glu Gly Cys Gln Gln Ile Ile Arg Gln Leu
            50                  55                  60

Gln Pro Ser Leu Gln Thr Gly Thr Glu Glu Leu Lys Ser Leu Tyr Asn
        65                  70                  75                  80

Thr Val Val Thr Leu Tyr Cys Val His Gln Arg Ile Asp Val Arg Asp
                        85                  90                  95

Thr Lys Glu Ala Leu Glu Glu Val Glu Lys Arg Gln Lys Asn Ser Gln
                        100                 105                 110

Gln Lys Ile Gln Gln Ala Ala Ala Asp Lys Glu Asn Ser Arg Gln Ile
                        115                 120                 125

Ser Gln Asn Tyr
                130
```

(2) INFORMATION FOR SEQ ID NO:114:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:114:

```
        Met Gly Ala Arg Ala Ser Val Leu Ser Gly Gly Glu Leu Asp Arg Trp
        1               5                   10                  15

Glu Lys Ile Arg Leu Arg Pro Gly Gly Lys Lys Tyr Lys Leu Lys
                     20                  25                  30

His Ile Val Trp Ala Ser Arg Glu Leu Glu Arg Phe Ala Val Asn Pro
                         35                  40                  45

Gly Leu Leu Glu Thr Ser Glu Gly Cys Arg Gln Ile Met Gly Gln Leu
            50                  55                  60

Gln Pro Ser Leu Gln Thr Gly Thr Glu Glu Leu Lys Ser Leu Tyr Asn
        65                  70                  75                  80

Thr Val Val Thr Leu Tyr Cys Val His Gln Lys Ile Asp Val Arg Asp
                        85                  90                  95

Thr Lys Glu Ala Leu Glu Glu Val Glu Lys Arg Gln Lys Ile Ser Gln
                        100                 105                 110

Gln Lys Ile Gln Gln Ala Ala Xaa Asp Lys Glu Asn Ser Arg Gln Val
                        115                 120                 125

Ser Gln Asn Tyr
                130
```

(2) INFORMATION FOR SEQ ID NO:115:

(i) SEQUENCE CHARACTERISTICS:
        (A) LENGTH: 133 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:115:

```
        Met Gly Ala Arg Ala Ser Ile Leu Ser Gly Gly Lys Leu Asp Ala Trp
        1               5                   10                  15
```

```
    Glu Arg Ile Arg Leu Arg Pro Gly Gly Lys Lys His Tyr Lys Met Lys
                    20                  25                  30

His Leu Val Trp Ala Ser Arg Glu Met Glu Arg Phe Ala Leu Asn Pro
                35                  40                  45

Gly Leu Leu Glu Thr Ala Glu Gly Cys Gln Gln Ala Met Gly Gln Ile
            50                  55                  60

Gln Pro Ala Leu Gln Thr Gly Thr Glu Glu Leu Arg Ser Leu Tyr Asn
    65                  70                  75                  80

Thr Ile Ala Thr Ile Tyr Cys Val Xaa Gln Lys Ile Glu Val Arg Asp
                    85                  90                  95

Thr Lys Glu Ala Leu Glu Glu Val Glu Lys Arg Gln Lys Lys Ser Lys
                    100                 105                 110

Gln Lys Ile Gln Gln Ala Ala Arg Asp Glu Gly Asn Asn Ser Gln Val
                115                 120                 125

Ser Gln Asn Tyr Phe
            130
```

(2) INFORMATION FOR SEQ ID NO:116:

(i) SEQUENCE CHARACTERISTICS:
        (A) LENGTH: 132 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:116:

```
    Met Gly Ala Arg Ala Ser Val Leu Ser Gly Gly Lys Leu Asp Ala Trp
    1               5                   10                  15

Glu Lys Ile Arg Leu Arg Pro Gly Gly Lys Lys Gln Tyr Lys Met Lys
                    20                  25                  30

His Leu Val Trp Ala Ser Arg Glu Leu Glu Arg Phe Ala Ile Asn Pro
                35                  40                  45

Gly Leu Leu Glu Thr Ala Glu Gly Cys Leu Asp Ile Ile Glu Gln Leu
            50                  55                  60

Gln Pro Thr Leu Lys Thr Gly Ser Glu Glu Leu Gln Ser Val Tyr Asn
    65                  70                  75                  80

Leu Val Thr Thr Leu Phe Cys Val His Gln Arg Ile Asp Val Lys Asp
                    85                  90                  95

Thr Lys Glu Ala Leu Glu Glu Val Glu Lys Val Arg Lys Asn Lys Gln
                    100                 105                 110

Gln Lys Ala Gln Gln Ala Ala Met Ala Lys Gly Asn Ser Ser Gln Val
                115                 120                 125

Ser Gln Asn Tyr
            130
```

(2) INFORMATION FOR SEQ ID NO:117:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:117:

AAAGAAGCTT TAGATNAANT AGAGGANATA CAAAANAAGA GCGGGCAAAA GACA        54

(2) INFORMATION FOR SEQ ID NO:118:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:118:

AAGGAAGCTT TAGATAAAAT AGAGGAAGTA CAGAGAAAGA GCAAGCAAAA GACA      54

(2) INFORMATION FOR SEQ ID NO:119:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:119:

AAGGAAGCTT TAGATAAGAT AGAGGAAGAG CAAAACAAAA GTAAGAAAAA AGCA      54

(2) INFORMATION FOR SEQ ID NO:120:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:120:

AAGGAAGCTC TAGAGAAGGT AGAGGAAGAG CAAAACAAAA GTAAGAAAAA AGCA      54

(2) INFORMATION FOR SEQ ID NO:121:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:121:

AAGGAAGCTT TAGAGAAGAT AGAGGAAGAG CAAAACAAAA GTAAGAAAAA AGCA      54

(2) INFORMATION FOR SEQ ID NO:122:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO:122:

AAGGAGGCTT TAGAGAAGAT AGAGGAAGAG CAAAACAAAA GTAAGAAAAA GGCA      54

(2) INFORMATION FOR SEQ ID NO:123:

(i) SEQUENCE CHARACTERISTICS:
        (A) LENGTH: 54 base pairs
        (B) TYPE: nucleic acid

```
            (C) STRANDEDNESS: single
            (D) TOPOLOGY: linear (ii) MOLECULE TYPE: DNA (genomic)

(xi) SEQUENCE DESCRIPTION: SEQ ID NO:123:

AAGGAAGCTT TAGAAAAGAT AGAGGAAGAG CAAAACAAAA GTAAGAAAAA AGCA           54

(2) INFORMATION FOR SEQ ID NO:124:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:124:

AAGGAAGCTT TAGATAAGAT AGAGGAAGAG CAAAACAAAA GTAAGAAAAA AGCN           54

(2) INFORMATION FOR SEQ ID NO:125:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:125:

AAGGAAGCTT TAGACAAGAT AGAGGAAGAG CAAAACAAAA GTAAGAAAAA AGCA           54

(2) INFORMATION FOR SEQ ID NO:126:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:126:

AAGGAAGCCT TAGAGAAGAT AGAGGAAGAG CAAAACAAAA GTAAGAAAAA GGCA           54

(2) INFORMATION FOR SEQ ID NO:127:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:127:

AAGGAAGCTT TAGAGAAGAT AGAGGAAGAG CAAAACAAAA GTAAAGAAAA AGCA           54

(2) INFORMATION FOR SEQ ID NO:128:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: DNA (genomic)
```

-continued (xi) SEQUENCE DESCRIPTION: SEQ ID NO:128:

AAGGAAGCTT TAGATAAGAT AGAGGAAGAG CAAAACAAAA GTAAGAAAAA AGCA        54

(2) INFORMATION FOR SEQ ID NO:129:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:129:

AAGGAAGCTT TAGATAAGNT AGAGGAAGAG CAAAACAAAA GTAAGAAAAA GGAA        54

(2) INFORMATION FOR SEQ ID NO:130:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:130:

AAAGAAGCTC TAGAGGAAGT GGAAAAGAGA CAAAAGAACA GTCAGCAAAA AATA        54

NUCLEIC ACID FRAGMENTS DERIVED FROM THE HIV-1 VIRUS GENOME, CORRESPONDING PEPTIDES AND THEIR APPLICATIONS AS REAGENTS FOR EVALUATION OF THE RISK OF MATERNOFOETAL TRANSMISSION OF HIV-1

FIELD OF THE INVENTION

The present invention relates to nucleic acid fragments derived from the genome of the human immunodeficiency virus type 1 (HIV-1), as well as to the corresponding peptides and to their applications as reagents for screening and evaluation of the risk of maternofoetal transmission of HIV-1.

BACKGROUND OF THE INVENTION

Two distinct types of HIV (human immunodeficiency virus: HIV-1 and HIV-2) have been described and are the agents responsible for AIDS. Analysis of their nucleic acid sequence has enabled different HIV-1 subtypes to be identified, although it has not been possible to establish any correlation between the variability and the pathogenicity.

The analysis of nucleotide fragments of different HIV-1 isolated has shown the existence, via analysis of the env gene, of at least 7 different subtypes designated A to G (MYERS G. et al., Human retroviruses and AIDS, 1993, Los Alamos Nat. Lab.).

More recently, another two isolates, considered to be markedly further away from the other 7 subtypes, that is to say whose sequence homology is furthest from that of the HIV-1 reference strains, have also been isolated and have been assigned to a new HIV-1 group, the O group, as opposed to the M group corresponding to the abovementioned 7 subtypes A–G, in view of their genomic organization (5' LTR Gag Pol Vif Vpu Vpr Tat Rev Env Nef LTR 3').

In view of the number of subjects suffering from HIV-1 and the mode of transmission of this virus (sexual and via blood), it was urgent to have at one's disposal both diagnostic reagents and immunogenic compositions capable of inducing the formation of neutralizing antibodies.

A number of peptides have been proposed for this purpose, originating, in particular, from the env protein or the gag protein.

As regards the gag protein, and more especially the p17 protein (included in the p55 protein), the prior art mentions a number of peptides which have been selected in the said p17 protein of HIV-1, for their diagnostic and/or vaccinal value.

There may be mentioned, for example:
International Application PCT WO 91/08227 (REPLICO AB), which relates to peptides originating from the p17 protein of HIV-1 and which essentially make it possible to discriminate between false positives and true positives. These peptides comprise the epitopes present at positions 118–132 of the p17 protein of HIV-1 (C-terminal position);
U.S. Pat. No. 5,185,147 (L. D. PAPSIDERO) mentions small peptides (11 amino acids or less) which are the only ones to react with monoclonal antibodies capable of neutralizing the biological activity of HIV-1, and which are advantageous for diagnostic or vaccinal purposes (immunogenic properties). These various peptides correspond to positions 12–22 of the p17 protein;
European Patent Application 0,426,314 (VIRAL TECHNOLOGIES INC and THE GEORGE WASHINGTON UNIVERSITY) mentions 5 major segments of the p17 protein of HIV-1, displaying potentially important immunogenic epitopes: peptide A (1–32), peptide B (33–50), peptide C (51–84), peptide D (85–114) and peptide E (114–131), and recommends the use of peptides A, B, C and E for the detection of HIV-1 and the use of peptides A, B, C, D and E for the preparation of an immunogenic composition.

However, the collective peptides of the prior art do not solve the crucial problem of the evaluation of the risk of maternofoetal transmission of HIV-1.

Now, in 1995, the maternofoetal transmission of HIV-1 constitutes a major public health problem, since its progression goes hand in hand with that of the contamination with HIV-1 throughout the world.

The World Health Organization (WEO) estimates at more than one million the number of children contaminated worldwide.

In France, the number of women of child-bearing age who are seropositive for HIV-1 is estimated at 30,000–40,000.

The degree of vertical transmission is from 15 to 25% in both Europe and the USA. This degree is higher on the African continent, ranging from 20 to 40% for reasons which are not very clear, doubtless as a result of coinfection of the mother and breast-feeding.

Putting European and American pregnant women on Retrovir$^{(R)}$ (AZT) until they give birth has enabled the degree of transmission to be reduced to 8.3%.

Twelve years after the discovery of the virus, our ignorance of the physiopathology of the vertical transmission is still considerable: many arguments indicate that transmission of the virus from mother to foetus may take place at a late stage in utero (in the last two months), at the time of delivery with a probably greater incidence and during breast-feeding, which is consequently strongly discouraged.

Among the parameters which may influence the vertical transmission, few have, at the present time, been demonstrated as being positively correlated with the risk of transmission. These are:
an advanced stage of the disease in the mother (grade IV),
a positive P24 antigenaemia, and/or a CD4+ lymphocyte level of less than 200/mm$^3$,
a high plasma viraemia in the mother.

The absence of one of these parameters does not, however, rule out the risk of vertical transmission, it merely decreases it.

In contrast, the presence of neutralizing antibodies in the mother, protecting passage to the child, remains very controversial.

Among the virological factors of biological expression (degree of replication, cellular tropism, cytotoxicity, capacity for induction of syncytia) or molecular factors of biological expression (in particular in the gene coding for the gp120 envelope glycoprotein), none has, to date, been demonstrated as being able to influence the risk of vertical transmission (P. ROQUES et al., AIDS, 1993, 7 (suppl. 2), S39–S43; F. X. MBOPI KEOU et al., Bull. Inst. Pasteur, 1994, 92, 3–18; Y. F. KHOURI et al., J. Clin. Invest., 1995, 95, 732–737; G. A. MULDER-KAMPINGA et al., Journal of Virology, 1995, 69, 2285–2296).

It was consequently the object of the present invention to provide for nucleic acid fragments and the corresponding peptides capable of serving as reagents for detection and evaluation of the risk of maternofoetal transmission of HIV-1.

SUMMARY OF THE INVENTION

The subject of the present invention is a nucleic acid fragment originating from the gene coding for a fragment of the p17 matrix protein of HIV-1, essentially consisting of 21 to 90 nucleotides and including at least the sequence represented by the formula Y5 Y6 Y7 Y8 Y9 Y10 Y11, in which:

Y5 represents AAA, AAG, GAA,

Y6 represents ATA, TTA, CTG, GTA, CTA, GTG, ATG,

Y7 represents GAG, GAA,

Y8 represents GAA, AAG,

Y9 represents ATA, GTA, CTA, GAA, GAG, GAC, GAT, AGA,

Y10 represents CAA, CAG, CGA,

Y11 represents AAA, AGT, AAG, AAT, CAT, AAC,ACC, on condition that, when Y5 represents AAA or AAG, Y6 is other than ATA, Y7 is other than GAG or GAA, Y8 is other than GAA, Y9 is other than GAG or GAA, Y10 is other than CAA or CAG and Y11 is other than AAT or AAC.

Such a sequence codes for a fragment of the p17 matrix protein of HIV-1 consisting of 7 to 30 amino acids and including at least the amino acid sequence 103–109 of the said protein.

According to an advantageous embodiment of the said nucleic acid sequence, it possesses the following formula:

Y1 GAA Y2 Y3 Y5 Y5 Y6 Y7 Y8 Y9 Y10 Y11 Y12 Y13 Y15 Y15 Y16 Y17 in which

Y5–Y11 have the same meaning as above, and

Y1 represents AAA, AAG,

Y2 represents GCT, GCC,

Y3 represents TTA, CTA,

Y4 represents GAT, GAC, GAG,

Y12 represents AGG, AAG, AAA, ATC, AAC,

Y13 represents AGC, AAC, AGT, AAG,

Y14 represents GGG, AAG, AAA, CAG,

Y15 represents CAA, AAA, AGA,

Y16 represents AAG, AAA, ACA, CAA, AAC, AAT,

Y17 represents ACA, GCA, AGC, ATA, GCC, GCT, GCG.

Preferably, the said sequence is selected from the following sequences:

AAA GAA GCT TTA GAT AAA ATA GAG GAA ATA CAA AAA AGG AGC GGG CAA AAG ACA SEQ ID No. 1 (DIA)

AAA GAA GCC TTA GAC AAA ATA GAG GAA ATA CAA AGT AAG AAC AAG CAA AAG GCA SEQ ID No. 2 (MAM)

AAG GAA GCT TTA GAT AAA ATA GAG GAA GTA CAG AAA AAG AGC AAG CAA AAG ACA SEQ ID No. 3 (MOU)

AAG GAA GCC TTA GAT AAA ATA GAG GAA ATA CAA AAG AAG AGC AAG CAA AAG ACA SEQ ID No. 4 (BAB)

AAG GAA GCT TTA GAT AAA TTA GAG GAA ATA CAA AAT AAG AGC AAA CAA AAG ACA SEQ ID No. 5 (DOS)

AAG GAA GCT TTA GAT AAG CTG GAG GAA ATA CAA CAT AAG AAC AAG CAA AAG ACA SEQ ID No. 6 (LAN)

AAG GAA GCC TTA GAT AAA ATA GAG GAG ATA CAA AAT AAG AGC AAG CAA AAA ACA SEQ ID No. 7 (FRA)

AAG GAA GCT TTA GAT AAA ATA GAG GAA CTA CAA

AAG AAG AGT AAG CAA AAA GCA SEQ ID No. 8 (WAN)

AAG GAA GCT TTA GAT AAG ATA GAG GAA GAA CAA AAC AAA AGT AAG AAA AAA GCA SEQ ID No. 9 (ABD)

AAG GAA GCT TTA GAT AAG ATA GAG GAA GAG CAA AAC AAA AGT AAG AAA AAA GCA SEQ ID No. 10 (ARI)

AAG GAA GCT TTA GAG AAG ATA GAG GAA GAG CAA AAC AAA AGT AAG AAA AAG GCA SEQ ID No. 11 (BOI)

AAG GAA GCT TTA GAG AAG ATA GAG GAA GAG CAA AAC AAA AGT AAG AAA AAA GCASEQ ID No. 12 (DUM)

AAG GAA GCT TTA GAT AAG ATA GAG GAA GAG CAA AAC AAA AGT AAG AAA AAA GCA SEQ ID No. 13 (PAL)

AAG GAA GCT TTA GAC AAG ATA GAA GAA GAG CAA AAC AAA AGT AAG AAA AAA GCA SEQ ID No. 14 (RYO)

AAG GAA GCT TTA GAG AAG ATA GAG GAA GAG CAA AAC AAA AGT AAG AAA ACA AGC SEQ ID No. 15 (FLO)

AAG GAA GCT TTA GAG AAG ATA GAG GAA GAG CAA AAC AAA AGT AAG AAA CAA GCA SEQ ID No. 16 (4501)

AAG GAA GCT TTA GAG AAG ATA GAG GAA GAG CAA AAC AAA AGT AAG AAA AAA GCA SEQ ID No. 17 (FAL)

AAG GAA GCT CTA GAG AAG GTA GAG GAA GAG CAA AAC AAA AGT AAG AAA AAN GCASEQ ID No. 18 (HAR)

AAG GAA GCT TTA GAC AAG ATA GAG GAA GAA CAA AAC AAA AGT AAG AAA AAA GCA SEQ ID No. 19 (RIV)

AAG GAA GCT TTA GAG AAG ATA GAG GAA GAG CAA AAC AAA AGT AAG AAA AAG GCASEQ ID No. 20 (CHET)

AAG GAA GCT TTA GAG AAG GTA GAG GAA GAG CAA ACC AAA AGT AAG AGA AAA GCA SEQ ID No. 21 (CEL)

AAG GAA GCT CTA GAC AAG ATA GAG GAA GAG CAA AAC AAA AGT AAG AAA AAG GCA SEQ ID No. 22 (SIW)

AAG GAA GCT TTA GAC AAG ATA GAG GAA GAG CAA ACC AAA AGT AAG AAA AAA GCASEQ ID No. 23 (MOE)

AAG GAA GCT TTA GAG AAG ATA GAG GAA GAN CAA ACC AAA AGT AAG AAA AAA GCA SEQ ID No. 24 (GOB)

AAG GAA GCT TTA GAG AAA GTA GAG GAA GAG CAA AAC AAA AGT AAG AAA AAG GCA SEQ ID No. 25 (4541)

AAG GAA GCT TTA GAG AAG GTA GAG GAA GAG CAA AAC AAA AGT AAG AAA AAA GCA (TM SEQ ID No. 26 (2754)

AAG GAA GCT TTA GAG AAG ATA GAG GAA GAG CAA AAC AAG AGT AAG AAA AAA GCA SEQ ID No. 27 (2826)

AAA GAA GCT CTA GAG GAA GTG GAA AAG AGA CAA AAG ATC AGT CAG CAA AAA ATA SEQ ID No. 28 (MPA)

AAA GAA GCT CTA GAG GAA GTG GAA AAG AGA CAA AAG ATC AGT CAG AAA AAA ATA SEQ ID No. 29 (IGN)

AAA GAA GCT CTA GAG GAA GTG GAA AAG GTA CGA AAA AAC AAG CAG CAA AAA GCA SEQ ID No. 30 (OSA)

AAG GAA GCT TTA GAG AAG ATG GAG GAA GAG CAA AAC AAA AGT AAG AAA AAA GCA SEQ ID No. 31 (BOU)

or a fragment of these sequences, such as:

| | |
|---|---|
| TTTTGTTTTGCTCTTCCTCTATCTT, | SEQ ID No. 32 (probe 1) |
| GTTTTGCTCTTCCTCTACC, | SEQ ID No. 33 (probe 2) |
| GGTTTGCTCTTCCTCTATA, | SEQ ID No. 34 (probe 3) |

GTTTGCTCTTCCTCTACCT, SEQ ID No. 35 (probe 4)

TTTTGTTTTGCTCTTCCTCTAC TTT, SEQ ID No. 56 (probe 5)

CTTTTGTTTTGCTCTTCTTCTA TCT. SEQ ID No. 57 (probe 6)

Nucleic acid sequence is understood to mean both the sequences as defined above and their complementary sequences.

The subject of the present invention is also the corresponding peptide sequences, that is to say the peptide sequences consisting of 7 to 30 amino acids and including at least the amino acid sequence 103 to 109 of the p17 viral matrix protein represented by the formula X2 X3 Glu X4 X5 X6 X7, in which:

X2 represents Lys, Glu

X3 represents Ile, Leu, Val, Met

X4 represents Glu, Lys

X5 represents Ile, Val, Glu, Art, Leu

X6 represents Gln, Arg, and

X7 represents Lys, Ser, Asn, His, Thr, on condition that, when X2 represents Lys, X3 is other than Ile, X4 and X5 are other than Glu, X6 is other than Gln and X7 is other than Asn.

According to an advantageous embodiment of the said sequence, it possesses the following formula:

Lys Glu Ala Leu X1 X2 X3 Glu X4 X5 X6 X7 X8 X9 X10 X11 X12 X13, in which

X2–X7 have the same meaning as above, and

X1 represents Asp, Glu

X8 represents Arg, Lys, Ile, Asn

X9 represents Ser, Asn, Lys

X10 represents Gly, Lys, Gln, Glu

X11 represents Gln, Lys, Arg

X12 represents Lys, Gln

X13 represents Thr, Ala, Ile.

Preferably, the said sequence is selected from the following sequences:

Lys Glu Ala Leu Asp Lys Ile Glu Glu Ile Gln Lys Arg Ser Gly Gln Lys Thr SEQ ID No. 36 (DIA)

Lys Glu Ala Leu Asp Lys Ile Glu Glu Ile Gln Ser Lys Asn Lys Gln Lys Ala SEQ ID No. 37 (MAM)

Lys Glu Ala Leu Asp Lys Ile Glu Glu Val Gln Lys Lys Ser Lys Gln Lys Thr SEQ ID No. 38 (MOU)

Lys Glu Ala Leu Asp Lys Ile Glu Glu Ile Gln Lys Lys Ser Lys Gln Lys Thr SEQ ID No. 39 (BAB)

Lys Glu Ala Leu Asp Lys Leu Glu Glu Ile Gln Asn Lys Ser Lys Gln Lys Thr SEQ ID No. 40 (DOS)

Lys Glu Ala Leu Asp Lys Leu Glu Glu Ile Gln His Lys Asn Lys Gln Lys Thr SEQ ID No. 41 (LAN)

Lys Glu Ala Leu Asp Lys Ile Glu Glu Ile Gln Asn Lys Ser Lys Gln Lys Thr SEQ ID No. 42 (FRA)

Lys Glu Ala Leu Asp Lys Ile Glu Glu Leu Gln Lys Lys Ser Lys Gln Lys Ala SEQ ID No. 43 (WAN)

Lys Glu Ala Leu Asp Lys Ile Glu Glu Glu Gln Asn Lys Ser Lys Lys Lys Ala SEQ ID No. 44 (ABD)

Lys Glu Ala Leu Glu Lys Ile Gln Glu Glu Gln Asn Lys Ser Lys Lys Lys Ala SEQ ID No. 45 (BOI)

Lys Glu Ala Leu Glu Lys Ile Glu Glu Glu Gln Asn Lys Ser Lys Lys Gln Ala SEQ ID No. 46 (4501)

Lys Glu Ala Leu Glu Lys Val Glu Glu Glu Gln Asn Lys Ser Lys Lys Lys Ala SEQ ID No. 47 (HAR)

Lys Glu Ala Leu Glu Lys Val Glu Glu Glu Gln Thr Lys Ser Lys Arg Lys Ala SEQ ID No. 48 (CEL)

Lys Glu Ala Leu Glu Lys Ile Glu Glu Glu Gln Asn Lys Ser Glu Lys Lys Ala SEQ ID No. 49 (SIW)

Lys Glu Ala Leu Asp Lys Ile Glu Glu Glu Gln Thr Lys Ser Lys Lys Lys Ala SEQ ID No. 50 (MOE)

Lys Glu Ala Leu Glu Lys Ile Glu Glu Glu Gln Thr Lys Ser Lys Lys Lys Ala SEQ ID No. 51 (GOB)

Lys Glu Ala Leu Glu Glu Val Glu Lys Arg Gln Lys Ile Ser Gln Gln Lys Ile SEQ ID No. 52 (MPA)

Lys Glu Ala Leu Glu Glu Val Glu Lys Arg Gln Lys Lys Ser Lys Gln Lys Ile SEQ ID No. 53 (IGN)

Lys Glu Ala Leu Glu Glu Val Glu Lys Val Arg Lys Asn Lys Gln Gln Lys Ala SEQ ID No. 54 (OSA)

Lys Glu Ala Leu Glu Lys Met Glu Glu Glu Gln Asn Lys Ser Lys Lys Lys Ala SEQ Id No. 55 (BOU)

Advantageously, the said peptides may be prepared by synthesis according to known methods.

Unexpectedly, the Applicant found that, depending on the subtype in question, these nucleic acid fragments and the peptides corresponding to them are significantly associated with the incidence of maternofoetal transmission of HIV-1.

In particular, the following (nucleic acid and peptide) sequences are considered to be transmissible:

| | subtype A | subtype B | subtype G |
|---|---|---|---|
| Nucleic acid sequences | SEQ ID No. 1 | SEQ ID NO. 9 | SEQ ID No. 28 |
| | SEQ ID No. 2 | SEQ ID No. 11 | SEQ ID No. 30 |
| | SEQ ID No. 3 | | |
| Peptide sequences | SEQ ID No. 36 | SEQ ID No. 44 | SEQ ID No. 52 |
| | SEQ ID No. 37 | SEQ ID No. 45 | SEQ ID No. 54 |
| | SEQ ID No. 38 | | |

Such data demonstrate for the first time the association between the viral molecular markers and the presence of a high or low risk of maternofoetal transmission of HIV-1.

The subject of the present invention is also antipeptide antibodies as defined above.

According to an advantageous embodiment of the said antibodies, they consist of polyclonal antibodies.

According to another advantageous embodiment of the said antibodies, they consist of monoclonal antibodies.

The polyclonal antibodies are advantageously obtained by immunization of a suitable animal (mammalian or gallinaceous, in particular, and the like) with a peptide according to the invention, where appropriate coupled to a suitable protein such as bovine serum albumin (BSA) or KLH.

The monoclonal antibodies to peptide fragments are advantageously obtained in a manner known per se, by fusion of spleen cells of mice immunized with an antigen consisting of a peptide fragment as defined above, where appropriate coupled to a suitable protein such as BSA or KLH, with suitable myeloma cells.

The subject of the present invention is also a reagent for the screening and evaluation of the risk of maternofoetal transmission of HIV-1, characterized in that it is selected from the group consisting of the nucleotide sequences, the peptide fragments and the antipeptide antibodies according to the invention.

In particular, the said reagent advantageously consists either of a set of peptides, or of a set of antipeptide antibodies according to the invention, or of a set of nucleotide sequences, as are defined above.

According to an advantageous embodiment of the invention, when the said reagent consists of at least one nucleic acid sequence, it comprises at least one sequence coding for amino acids 103–109 of the p17 protein of HIV-1, which nucleic acid sequence is represented by the formula Y5 Y6 Y7 Y8 Y9 Y10 Y11, in which:

Y5 represents AAA, AAG, GAA,

Y6 represents ATA, TTA, CTG, GTA, CTA, GTG, ATG,

Y7 represents GAG, GAA,

Y8 represents GAA, AAG,

Y9 represents ATA, GTA, CTA, GAA, GAG, GAG, GAT, AGA,

Y10 represents CAA, CAG, CGA,

Y11 represents AAA, AGT, AAG, AAT, CAT, AAC, or it is capable of specifically detecting a nucleic acid sequence containing the said formula.

According to this embodiment, the said reagent is selected, in particular, from the group consisting of the nucleotide sequences or fragments of the latter, as are defined above, which sequences are combined with at least one suitable means of detection.

Among the especially advantageous fragments of nucleic acid sequences, there may be mentioned:

```
        -    probe   1  (SEQ ID No. 32):
TTTTGTTTTGCTCTTCCTCTATCTT,
        -    probe   2  (SEQ ID No. 33):
GTTTTGCTCTTCCTCTACC,
        -    probe   3  (SEQ ID No. 34):
GGTTTGCTCTTCCTCTATC,
        -    probe   4  (SEQ ID No. 35):
GTTTGCTCTTCCTCTACCT,
        -    probe   5  (SEQ ID No. 56):
TTTTGTTTTGCTCTTCCTCTACTTT,
        -    probe   6  (SEQ ID No. 57):
CTTTTGTTTTGCTCTTCTTCTATCT,
``` which are especially specific for screening and evaluating the risk of transmission of HIV-1 in subtype B.

The probe 1 enables at least the sequence ARI (SEQ ID No. 10), BAR and BOI (SEQ ID No. 11) to be detected, the probe 2 enables at least the sequences HAR (SEQ ID No. 18), LOUB, VIL and 2754 (SEQ ID No. 26) to be detected, the probe 3 enables at least the sequences FAL (SEQ ID No. 17), HMI, AMO, CHET (SEQ ID No. 20), GOB (SEQ ID No. 24), MOE (SEQ ID No. 23), SIW (SEQ ID No. 22), FLO (SEQ ID No. 15), 2758, 2836 (SEQ ID No. 27), 4501 (SEQ ID No. 16), 4538 and 5613 to be detected, the probe 4 enables at least the sequence CEL (SEQ ID No. 21) to be detected, the probe 5 enables at least the sequence 4541 (SEQ ID No. 25) to be detected and the probe 6 enables at least the sequence RYO (SEQ ID No. 14) to be detected.

The other sequences are shown in FIG. 7.

The label is advantageously chosen from the group which comprises, in particular, radioactive isotopes, suitable enzymes, fluorochromes and suitable chemical labels.

According to another advantageous embodiment of the invention, when the said reagent consists of at least one peptide, it comprises at least one amino acid sequence 103–109 of the p17 protein of HIV-1, represented by the formula X2 X3 Glu X4 X5 X6 X7, in which:

X2 represents Lys, Glu

X3 represents Ile, Leu, Val, Met

X4 represents Gly, Lys

X5 represents Ile, Val, Glu, Arg

X6 represents Glu, Arg and

X7 represents Lys, Ser, Asn, His, Thr or it is capable of specifically detecting a peptide containing the said formula.

The subject of the present invention is also a method for the detection, screening and evaluation of the risk of maternofoetal transmission of HIV-1, in a biological sample, characterized in that it comprises a step in which the biological sample is brought into contact with a reagent according to the invention, and a step in which a specific interaction is detected between the said reagent and one or more sequences of the DNA of the said virus, consisting of one of the nucleic acid sequences as defined above and which are present in the said biological sample.

According to a preferred embodiment of this method, the detection of one of the sequences as defined above is performed after amplification by the PCR method of amplification (chain amplification by Taq polymerase with suitable primers) of the region coding for the p17 viral matrix protein, followed by hybridization of the product obtained on a membrane to which one or more of the probes as defined above have previously been bound.

The subject of the present invention is, in addition, a ready-to-use kit, outfit or coordinated set for carrying out the method for the detection, screening and evaluation of the risk of maternofoetal transmission of HIV-1, according to the invention, characterized in that it comprises, as well as amounts of suitable buffers and reagents for carrying out the said detection, suitable doses of at least one nucleotide probe or probe fragment according to the invention.

According to the invention, when the said probe is selected from the sequences ID No. 32, 33, 34, 35, 56 or 57, the said kit is especially suitable for the detection, screening and evaluation of the risk of transmission of HIV-1 subtype B.

According to an advantageous embodiment of the kit or outfit according to the present invention, this kit or outfit contains the following components:

the reagents needed for performing a PCR amplification of DNA, suitable doses of primers specific for the p17 region of the gag gene of HIV-1, and at least one nucleotide sequence according to the invention, capable of hybridizing under stringent conditions with the portion of the sequence of the p17 region of the gag gene of HIV-1 comprising one of the nucleotide sequences as defined above.

For the purposes of the present invention, stringent conditions are, in particular, the following: hybridization in the presence of 5×SSPE, 0.5% SDS for 30 min at temperatures which depend on the Tm of each previously bound oligonucleotide probe (45 to 60° C.).

The subject of the present invention is also a method for the detection, screening and evaluation of the risk of maternofoetal transmission of HIV-1, characterized in that it consists in detecting one of the peptide sequences as defined above in a maternal biological sample, by bringing the said biological sample into contact with a pool of antibodies specific for the said various peptide sequences.

The subject of the present invention is also a method for the detection, screening and evaluation of the risk of maternofoetal transmission of HIV-1, characterized in that it consists in detecting one of the antipeptide antibodies as defined above in a maternal biological sample, by bringing the said biological sample into contact with a pool of peptides according to the invention.

According to an especially advantageous embodiment of this method, the said pool of peptides consists of the sequences ID Nos. 44, 45, 47, 48, 50 and 51.

Such detection and evaluation reagents and methods according to the invention make it possible, in fact, to evaluate the risk of maternofoetal transmission, inasmuch as the viruses containing some of the abovementioned sequences are never transmitted to the child during pregnancy, whereas others are transmitted in this fashion systematically, and in particular the sequences SEQ ID No. 44 and SEQ ID No. 45 (see also FIG. 3).

The subject of the present invention is, in addition, a ready-to-use kit, outfit or coordinated set for carrying out the method for the detection, screening and evaluation of the risk of maternofoetal transmission of HIV-1, according to the invention, characterized in that it comprises, as well as amounts of suitable buffers and reagents for carrying out the said detection, a suitable solid support appropriately coated with at least one ligand chosen from the group which comprises the peptides according to the invention and the antibodies according to the invention, at least one vial containing conjugates chosen from the group which comprises the conjugates of suitable enzyme with suitable antihuman Ig antibodies, in particular goat antibodies, and the conjugates of suitable enzyme with antipeptide antibodies according to the invention, and suitable amounts or doses of a suitable visualization substance.

BRIEF DESCRIPTION OF THE DRAWINGS

As well as the foregoing provisions, the invention also comprises other provisions which will become apparent from the description which follows, which refers to examples of implementation of the method which is the subject of the present invention and also to the attached drawings, wherein:

FIGS. 1A and 1B show the products obtained by PCR; FIG. 1A; agarose gel: the products obtained after PCR amplification of the gene coding for the p17 protein; FIG. 1B; localization of the primers used in the nested PCR reactions, FIG. 5 illustrates the genotypic differences between subtypes A, B, G and D, FIG. 6 illustrates the results obtained in the evaluation of the risk of maternofoetal transmission of HIV-1 subtype B, FIG. 7 shows the multiple alignment of the nucleotide sequences coding for the p17 protein of HIV-1 from different viral isolates and their correlation with maternofoetal transmission.

DETAILED DESCRIPTION OF THE INVENTION

Figure 1B:
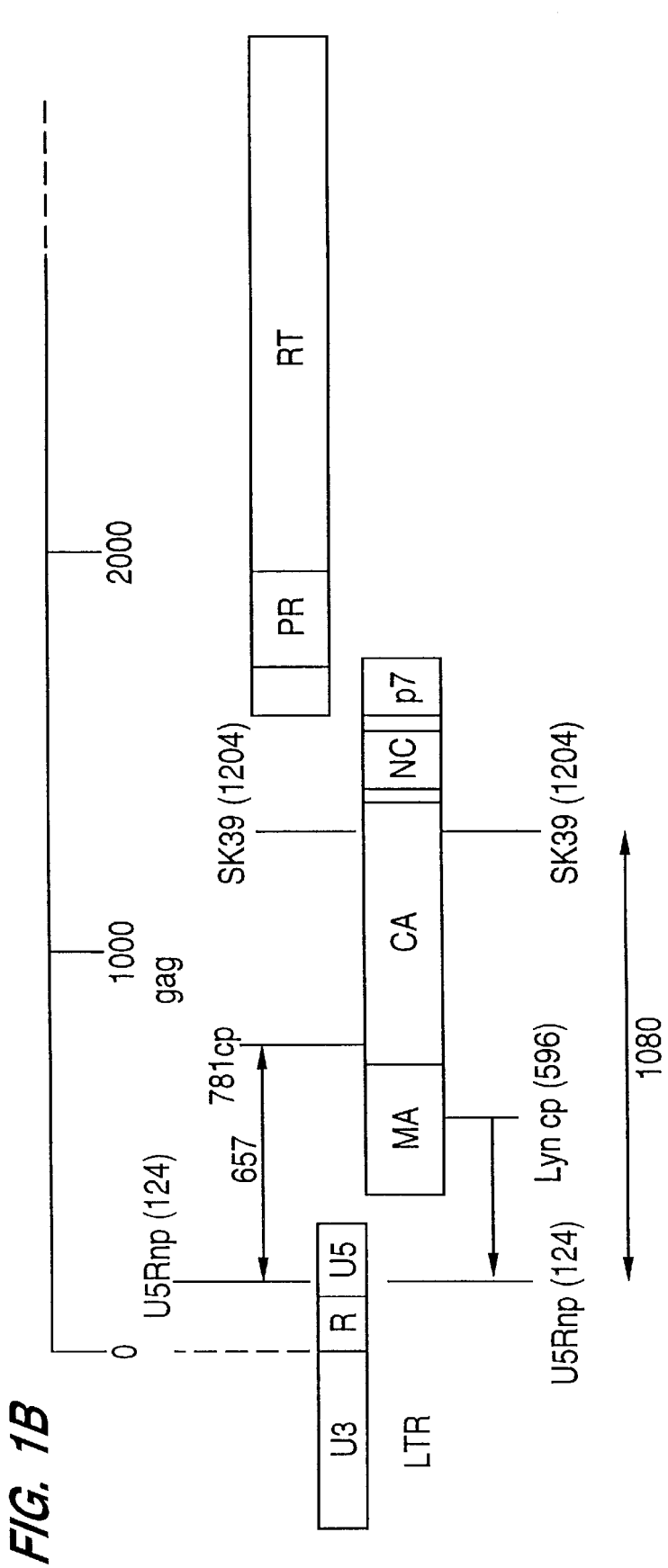

It should, however, by clearly understood that these examples are given only by way of illustration of the subject of the invention, and in no way constitute a limitation of the latter.

EXAMPLE 1

Rapid detection of material isolates of HIV-1 having a high or low risk of vertical transmission, by the reverse dot blot technique applied to the p17 (matrix protein) gene (technique employing a single PCR); application to subtype B.

1) Preparation of total cellular DNAs material, 5 to 10 ml of whole blood drawn onto anticoagulant (heparin or citrate), separation of the mononuclear cells from the peripheral whole blood of patients on a Ficoll gradient, lysis of the cells in 10 mM Tris-HCl buffer pH 7.8, 1 mM EDTA, 0.5% SDS with the addition of 20 mg/ml of proteinase K for 2 hours at 56° C., extraction of the nucleic acids with phenol, chloroform and isoamyl alcohol, precipitation in 3 M sodium acetate pH 5.4 and isopropanol (1 vol:10 vol), washing in 70% ethanol and dissolution in TE (10 mM Tris-HCl pH 7.5, 0.1 mM EDTA).

2) PCR amplification of the p17 gene sense primer: U5Rnp 5'-ACTCTGGTAGCTAGAGATCCCT-3'biotinylated at the 5' end, antisense primer: 781cp 5'-GGTGATATGGCCTGATGTACCAT-3' (781–759).

working protocol for 100 µl of final reaction volume: 10×PCR buffer (Appligene) containing 1.5 mM MgCl$_2$, 200 µM deoxynucleotides, 0.25 µM each primer, 0.6 U Taq polymerase (Appligene)/ml.

a step of 3 min at 94° C.; 38 cycles of 1 min at 57° C., 1 min at 72° C., 45 sec at 94° C.; a step of 2 min at 57° C. and 10 min at 72° C.

3) Preparation of the oligonucleotide probes 6 nucleotide probes of the respective sequences (5'–3'):

```
probe 1 (SEQ ID No. 32): TTTTGTTTTGCTCTTCCTCTATCTT,
probe 2 (SEQ ID No. 33): GTTTTGCTCTTCCTCTACC,
probe 3 (SEQ ID No. 34): GGTTTGCTCTTCCTCTATC,
probe 4 (SEQ ID No. 35): GTTTGCTCTTCCTCTACCT,
probe 5 (SEQ ID No. 56): TTTTGTTTTGCTCTTCCTCTACTTT,
probe 6 (SEQ ID No. 57): CTTTTGTTTTGCTCTTCTTCTATCT.
```

Surprisingly, the probes ID No. 32 and ID No. 57 enable HIV-1 viruses which are always transmitted to the foetus to be detected, whereas the probes 33, 34, 35 and 56 enable HIV-1 viruses which are never transmitted to the foetus to be detected.

Addition of a poly(dT) tail at the 3' end of each oligonucleotide probe:

200 pmol of each probe plus 80 nmol of dTTP in 100 µl of buffer (100 mM potassium cacodylate, 25 mM Tris-HCl, 1 mM CoCl$_2$, 0.2 mM DTT, pH 7.6) with 60 units (50 pmol) of terminal deoxyribonucleotidyl transferase (Boerhinger) for 60 min at 37° C. the reaction then being stopped by adding 100 µl of 10 mM EDTA.

4) Binding of the probes to membranes

Dilution of the probes in 100 μl of TE (10 mM Tris-HCl, 1 mM EDTA, pH 8), followed by binding to nylon membranes (Genetran-45) using a dot-blot apparatus (Bio-Dot, Biorad), followed by fixation with UV in a Spectrolinker oven (Spectronics Corporation) at an energy of 120 mJ/unit of surface.

Washing of the membranes in 200 ml of 5×SSPE (1×SSPE=180 mM NaCl, 10 mM NaH$_2$PO$_4$, 1 mM EDTA, pH 7.2) with 0.5% of SDS for 30 min at 55° C.

5) Hybridization of the PCR products on membranes

Denaturation of the PCR products for 3 min at 90° C., followed by hybridization in parallel with PCR controls of known sequences:

hybridization on membranes in 5×SSPE, 0.5% SDS for 30 min at temperatures that depend on the Tm of each oligonucleotide probe previously bound (45 to 60° C.), washing in 2×SSPE, 0.1% SDS at between 45 and 60° C.

6) Visualization by adding horseradish peroxidase HRP coupled to streptavidin, followed by a chemoluminescent substrate incubation of the membranes in 1 to 2 ml of 2×SSPE, 0.1% SDS containing 10 to 20 ml of HRP-streptavidin (5 mg/ml, Perkin-Elmer Cetus) for 15 min, followed by washing for 10 min in the same buffer, detection with chemoluminescent substrate.

7) Interpretation of the results

If a hybridization is obtained only with the probes 1 or 6 (probe 1 or 6 positive), and irrespective of the results obtained with the probes 2, 3, 4 and 5, there is a considerable risk of mother-child transmission.

If there is no hybridization in the presence of the probes 1 and 6 (probes 1 and 6 negative), and if the results obtained with the probe(s) 2 and/or 4 and/or 5 are positive, the risk is low.

If the probes 1, 2, 4 and 5 are negative (absence of hybridization and the probe 3 positive, the risk is probably low.

If all the probes are negative (absence of hybridization), a new sample should be tested. Should the result be confirmed, the maternal viral isolate belongs to an HIV-1 subtype other than subtype B.

EXAMPLE 2

Rapid detection of maternal isolates of HIV-1 having a high or low risk of vertical transmission, by the reverse dot blot technique applied to the p17 (matrix protein) gene (technique employing two successive PCR reactions: nested PCR reactions); application to subtype B.

1) Preparation of total cellular DNAs

The procedure is as in Example 1.

2) Amplification of the p17 gene by nested PCRs primary PCR: external primers sense primer: U5Rnp 5'-ACTCTGGTAGCTAGAGA TCCCT-3' (SEQ ID NO. 58)

antisense primer: SK39 5'-TTTGGTCCTTGTCTTATGT CCAGAATGC-3' SEQ ID NO. 60)

These primers correspond, respectively, to nucleotides 1–18 and 1204–1177 of the genome of HIV-1 strain LAI.

secondary PCR: internal primers sense primer: U5Rnp 5'-ACTCTGGTAGCTAGAGA (SEQ ID NO. 58) TCCCT-3' biotinylated at the 5' end (BioU5Rnp), antisense primer: 781cp 5'-GGTGATATGGCCTGATG TACCAT-3' (781–759) (SEQ ID NO. 61).

The working protocol is identical to that described in Example 1.

The secondary PCR is carried out on 2 μl of the primary PCR.

To identify the products amplified by the said PCR reactions, 5 μl of each sample are applied to a 1% agarose gel, an electrophoretic migration is run and the products are visualized by ethidium bromide staining. The results are illustrated in FIG. 1A, in which lane 1 corresponds to the molecular weight marker (digestion of øX174 with the enzyme Hind III); lanes 2 to 7 correspond, respectively, to 500, 250, 100, 50, 10 and 1 copies of the integrated provirus DNA extracted from 85-14 F2 cells, amplified with the primer pair U5Rnp-SK39; lanes 8 to 13 correspond to the products of the second PCR carried out with the primer pair BioU5Rnp-781cp on the product obtained with the first PCR (lanes 2 to 7); lanes 16 to 22 correspond to the products of PCR amplification of viral DNA of subtypes A, B, C, D, E, F and G, respectively, obtained using the primer pair BioU5Rnp-781cp (A=isolate BAB-MNT; B=isolate FAL-MNT; C=strain 15166; D=strain NDK; E=strain Viet 26; F=strain 1011; G=isolate MPA-M).

This figure shows that the limits of detection of the external and internal PCR reactions, determined using 85-14 F2 standard cells as specified above, are 10 and 1 copies, respectively.

FIG. 1B shows the position of the primer pairs used on the genome of HIV-1 strain LAI.

This set of primers is especially advantageous for amplifying all the isolates originating from HIV-1 subtypes A, B, C, D, E, F and G (FIG. 1A).

In similar fashion, for the detection of the isolates in maternal and foetal samples, the procedure is as specified in steps 3 to 7 of Example 1.

The interpretation of the results is identical to that of Example 1; however, the use of 2 nested PCR reactions makes the method more sensitive.

EXAMPLE 3

Rapid detection of mothers infected with HIV-1 having a high risk of vertical transmission, by the ELISA technique. (Detail of the working protocol for HIV-1 subtype B.)

1) Serum sampling material: 2 to 5 ml of the whole blood drawn into a dry tube separation of the blood clot by centrifugation storage of the sera in two aliquots in freezer tubes at −20° C.

2. Preparation of ELISA plates and positive controls 2-1) chemical synthesis of target peptides 6 peptides of the respective sequences (from N to C):

1 2 3 4 5 6 7 8 9 10 11 12 13 14 15 16 17 18

Lys Glu Ala Leu Glu Lys Ile Glu Glu Glu Gln Asn Lys Ser Lys
Lys Lys Ala                                    peptide 1 (SEQ ID No. 45)

Lys Glu Ala Leu Asp Lys Ile Glu Glu Glu Gln Asn Lys Ser Lys
Lys Lys Ala                                    peptide 2 (SEQ ID No. 44)

Lys Glu Ala Leu Glu Lys Val Glu Glu Glu Gln Asn Lys Ser Lys
Lys Lys Ala                                    peptide 3 (SEQ ID No. 47)

Lys Glu Ala Leu Glu Lys Ile Glu Glu Glu Gln Thr Lys Ser Lys
Lys Lys Ala                                    peptide 4 (SEQ ID No. 51)

Lys Glu Ala Leu Glu Lys Val Glu Glu Glu Gln Thr Lys Ser Lys
Arg Lys Ala                                    peptide 5 (SEQ ID No. 48)

Lys Glu Ala Leu Asp Lys Ile Glu Glu Glu Gln Thr Lys Ser Lys Lys Lys Ala    peptide 6 (SEQ ID No. 50)

An HIV non-specific peptide SP951481 is used as negative control (P–).

2-2) preparation of a pool of control antibodies

The pool of antibodies used is a pool of serum from seropositive patients.

2-3) binding of the peptides to an 8-well strip
- 2-3-1) material: 8-well strip (Costar Labcoat Amine Binding ref 2506)
  Dynatech Immulon 4 plate ref. 15415,
  peptide synthesized as described above.
  HIV non-specific peptide SP951481,
  a pool of viral antigens serving as positive controls of the anti-HIV response of the sera: lysate of cells chronically infected with HTL-VIII (50 million H9V3 cells lysed with 2 ml of a 1% solution of NP40 detergent),
  Gloria® skimmed milk,
  ortho-phenylenediamine in 30 mg tables (OPD, Sigma chimie, France),
  incubator at 37° C.,
  multichannel pipette
- 2-3-2) protocol
  dissolution of the peptides at a concentration of 2 mg/ml in a carbonate buffer pH 9.6 (50 mM NaHCO$_3$; 0.15 M NaCl). The peptides are diluted before use to a concentration of 2 μg/ml.
  100 μl of solution are distributed in each well in the following manner: the peptides 1 to 6 in wells 1 to 6, respectively; in well 7, an HIV non-specific peptide (SP951481) (P–) is introduced; lastly, in the well 8, the lysate of H9V3 (positive control of the anti-HIV response) diluted to 1/100 in PBS buffer (0.1 M phosphate pH 7.5, 0.15 M NaCl) (see FIG. 6).
  the plates (each sufficient to test 10 sera) are incubated for 2 hours at 37° C.
  the reagent is removed, and the plates are washed twice with 200 μl per well of a 0.05% Tween 20/PBS solution (buffer A).
  the plates are saturated (blocking of the non-specific binding of the antigens in the wells) by distributing 300 μl of a 3% solution of skimmed milk in 0.05% Tween 20/PBS, followed by incubation for 2 hours at 37° C.
  the plates are washed again as before.

The plates or strips may be stored, after desiccation, at 4° C.

3) ELISA 3-1) protocol
The sera to be tested, inactivated at 56° C. for 35 min, are diluted to 1/100 and to 1/1000 in buffer B: 0.05% Tween® 20/PBS; 3% skimmed milk (Gloria, Nestlé).

The pool of antibodies prepared as described in 2-2 is diluted to 1/1,000 in buffer B: solution C.

100 μl of each serum are distributed in the wells corresponding to the different antigens.

Absorption takes place in 1 hour at 37° C. in a humid atmosphere.

The wells are washed 3 times with buffer A.

The wells are saturated with 300 μl of the solution C, incubated for 1 h at 37° C. and washed 3 times with 0.1% Tween® 20/PBS.

100 μl of goat anti-human IgG serum (Cappel Organon Teknika Cat. Ref. 3201-0231) coupled to peroxidase, diluted to 1/10,000 in buffer B, are added.

5 washes are performed: 4 in 0.1% Tween 20/PBS and 1 in PBS alone.

3-2) visualization
into each well there are added 100 μl of a solution D: 0.05 M citrate buffer pH 5.6, and 0.01% H$_2$O$_2$, 3 mg/ml of ortho-phenylenediamine (OPD, Sigma chimie, France).

the plates are incubated for 30 min at room temperature in darkness.

the reaction is stopped with 50 μl of 4N sulphuric acid.

reading the optical density at 492 and 630 nm is performed with a plate reader (automated microplate reader EL311, Bio-Tek Instrument inc. USA).

3-3) Analysis of the results

An optical density of greater than 0.1 is considered to constitute a positive signal (detection of the corresponding peptide).

The determination of the presence of antibodies against the virus likely to be transmitted will correspond to a positive signal in wells 1 or 2 (see FIG. 6).

In the case of a positive signal in wells 1 or 2 and in either of wells 3 and 4: the mother still runs a higher risk of transmission.

A low risk of transmission will be validated if and only if there is a positive response of the mother's serum against any one of the peptides 3 to 6 (positive signal in one of wells 3 to 6) and no positive signal in wells 1, 2 and 7 or 8 (peptides 1, 2 and controls).

The risk will be considered to be non-evaluable if and only if there is no positive signal with any one of the peptides 1 to 6 in a test performed with at least two dilutions of the mother's serum.

In effect, there are a few cases of women not possessing anti-p17 antibodies, and the disappearance of these antibodies has been correlated with a progression in the disease. Hence, a positive response in wells 3 to 6 will be considered to be a good control of the validity of the test.

Table I below illustrates the same results quantitatively.

These results are expressed as the optical density of the 1/100 dilutions of different sera: positive control sera (C+) (pool of patients' sera), negative control sera (C–) and test sera, in the presence of the peptides 1 to 6, the control peptide (P–) and a virus lysate.

TABLE I

| Peptides tested and status | No. serum dilution | Control C+ 1/100 | sera C– 1/100 | 1st T VIL 51 1/100 | 2nd T VIL 52 1/100 | FAL 54 1/100 | BOU 55 1/100 | HAR 58 1/100 | FRA 57 1/100 | LEU 58 1/100 | LIN 59 1/100 | GOB 29 1/100 | HMI 30 1/100 |
|---|---|---|---|---|---|---|---|---|---|---|---|---|---|
| P(–) |   | 0.00 | 0.00 | 0.00 | 0.00 | 0.00 | 0.00 | 0.00 | 0.00 | 0.00 | 0.00 | 0.00 | 0.00 |
| P1* | T | 0.23 | 0.00 | –0.26 | 0.28 | 0.58 | 0.50 | 0.48 | 0.42 | 0.26 | 0.18 | 0.13 | –0.07 |

TABLE I-continued

| Peptides tested and status | No. serum dilution | Control C+ 1/100 | sera C− 1/100 | 1st T VIL 51 1/100 | 2nd T VIL 52 1/100 | FAL 54 1/100 | BOU 55 1/100 | HAR 58 1/100 | FRA 57 1/100 | LEU 58 1/100 | LIN 59 1/100 | GOB 29 1/100 | HMI 30 1/100 |
|---|---|---|---|---|---|---|---|---|---|---|---|---|---|
| P2 | T | 0.33 | 0.00 | 0.21 | −0.15 | 0.17 | 0.06 | −0.01 | −0.01 | −0.02 | −0.03 | 0.02 | −0.06 |
| P3 | NT | 0.27 | 0.00 | 0.22 | 0.18 | 0.05 | −0.01 | 0.02 | −0.03 | −0.03 | −0.06 | −0.04 | −0.06 |
| P6 | NT | 0.40 | 0.00 | 0.15 | 0.29 | 0.20 | 0.28 | 0.38 | 0.21 | 0.04 | 0.00 | 0.09 | −0.08 |
| P4 | NT | 0.30 | 0.00 | 0.85 | 0.18 | 0.15 | 0.06 | 0.01 | 0.00 | −0.02 | −0.01 | −0.04 | −0.09 |
| P5 | NT | 0.29 | 0.00 | 0.74 | 0.62 | 0.01 | 0.01 | 0.03 | 0.04 | 0.00 | −0.04 | 0.01 | 0.00 |
| H9V3 lysate(+) | | 0.38 | 0.00 | 0.52 | 0.53 | 0.37 | 0.44 | 0.14 | 0.05 | 0.01 | 0.07 | 0.19 | 0.67 |
| Peptides recognized | | | | P3, P4 P5, P6 | P1, P3, P4, P5, P6 | P1, P2 P4, P6 | P1, P8 | P1, P6 | P1, P6 | P1 | P1 | P1, P6 | — |
| Status of transmission deduced from the OD readings | | | | NT | NT | NT | NT | NT | T | T | T | T | 77 |
| Status of transmission observed [from study of the cohort] | | | | NT | NT | NT | NT | NT | NT | T | NT | NT | NT |

*P1 = peptide 1, P2 = peptide 2, etc
1st T = 1st trimester of pregnancy
2nd T = 2nd trimester of pregnancy 4) Demonstration of the correlation of the maternofoetal transmission of HIV with the sequences described above and identified in Examples 1 and 2

The following information was provided by the sequencing of viruses obtained from a control cohort:

HIV sequences isolated from different mothers and children were sequenced by the solid-phase direct sequencing method from 12 (HIV-1-infected mother)-child pairs, 4 children, 4 transmitting mothers and 22 non-transmitting mothers.

The blood samples are collected at the time of delivery for the mothers and during the first month of life for the children.

Figure 2:
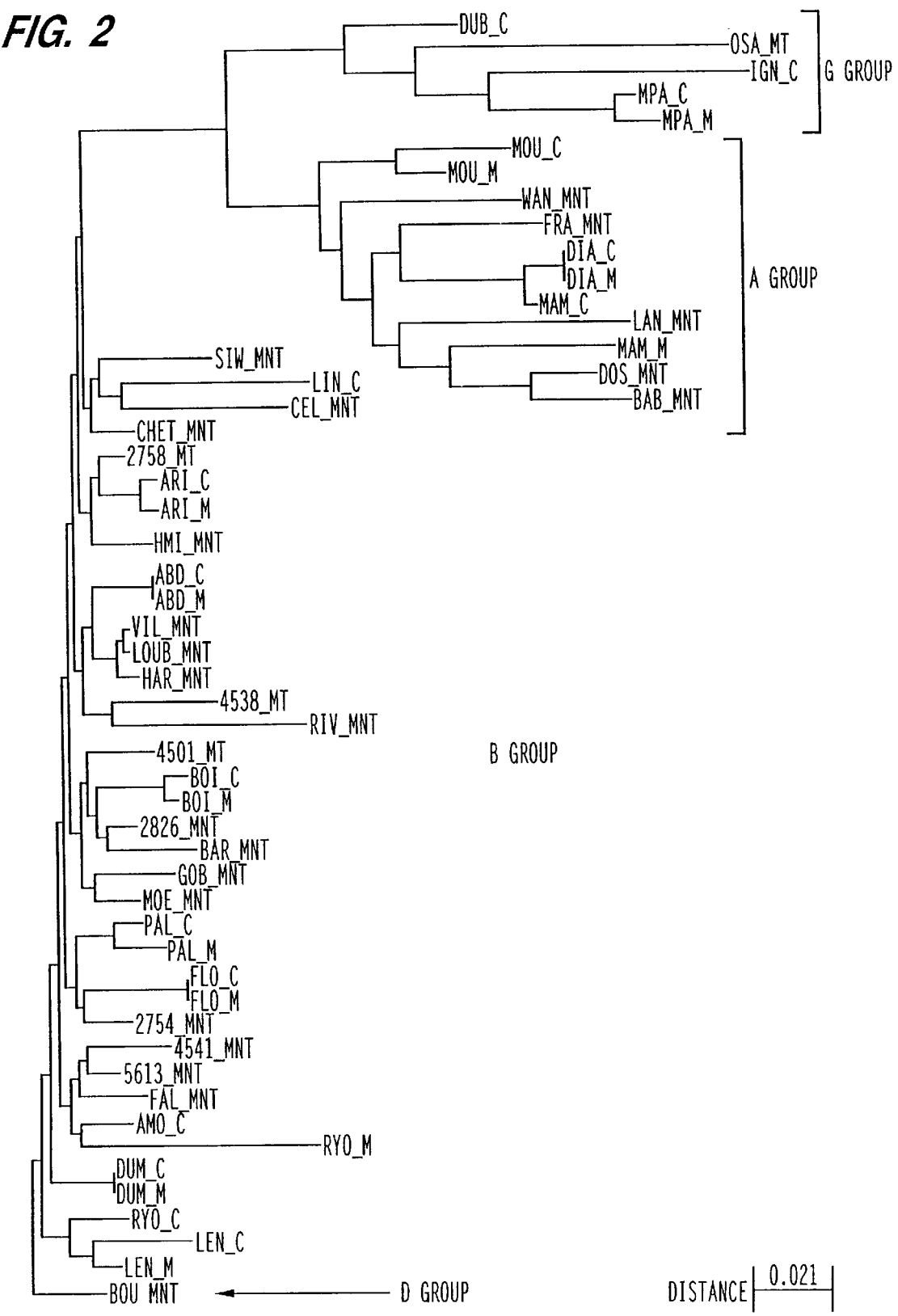
FIG. 2 shows the consensus phylogenetic tree of the nucleotide sequences.

In FIG. 2, a phylogenetic tree shows the distribution of the consensus DNA sequences in several clades. In almost all the mother-child pairs, the sequence of the isolate appearing in the child is closer to the sequence of its mother's isolate than to any other sequence, showing the genetic link existing in each pair.

Figure 3A:
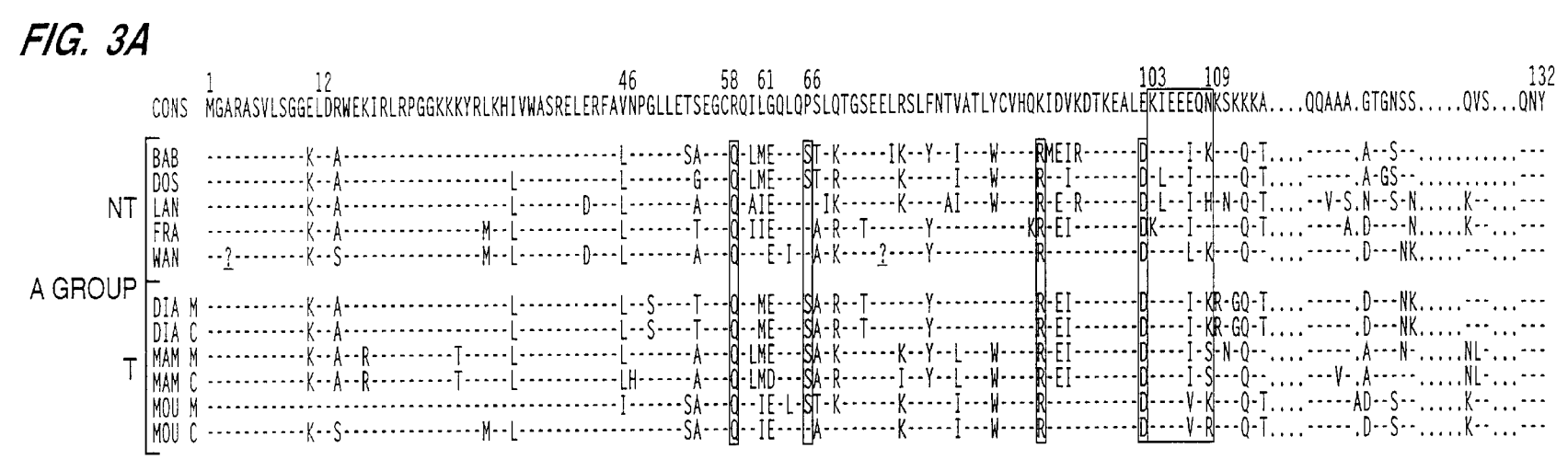
Figure 3B:
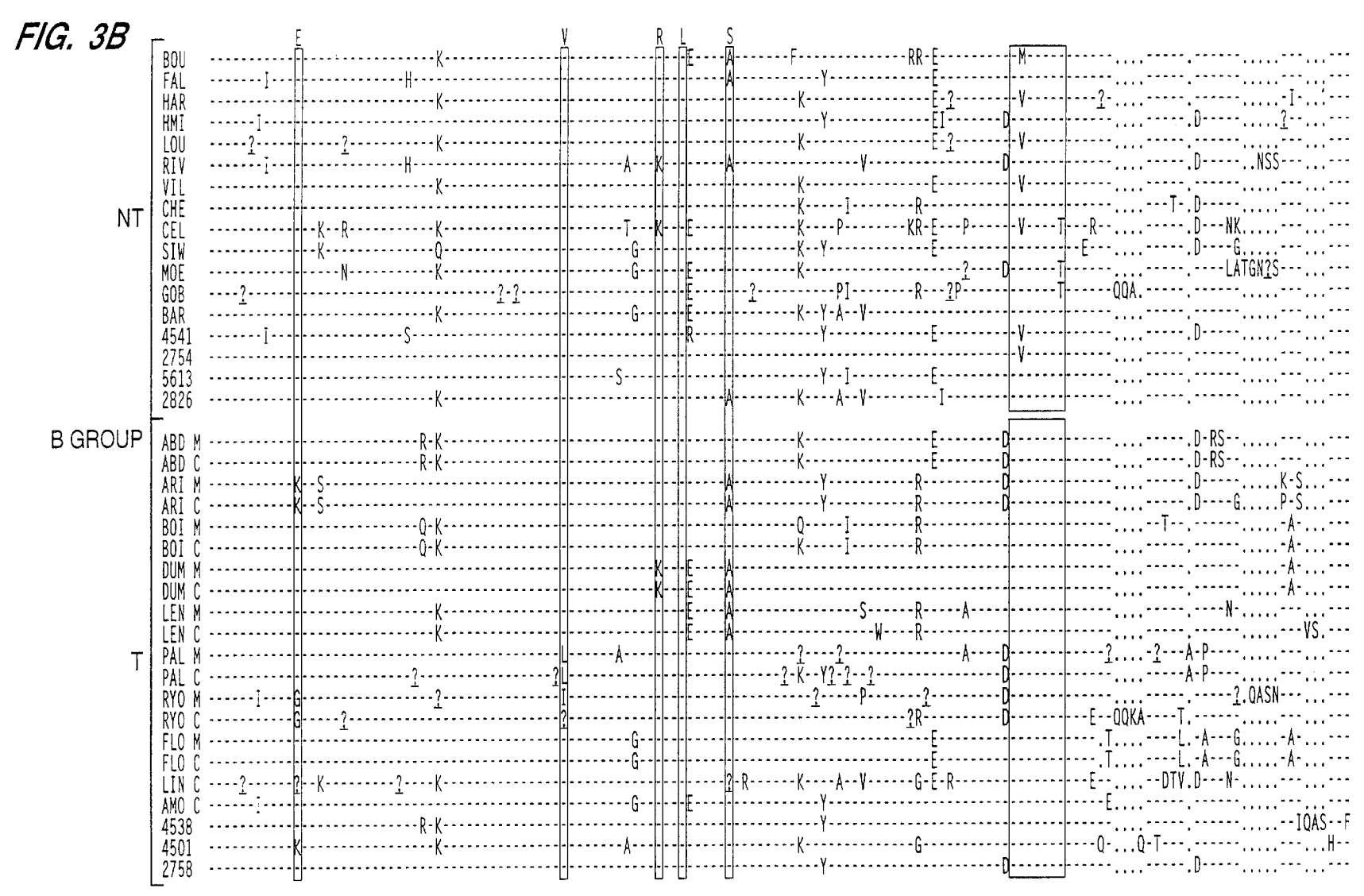
Figure 3C:
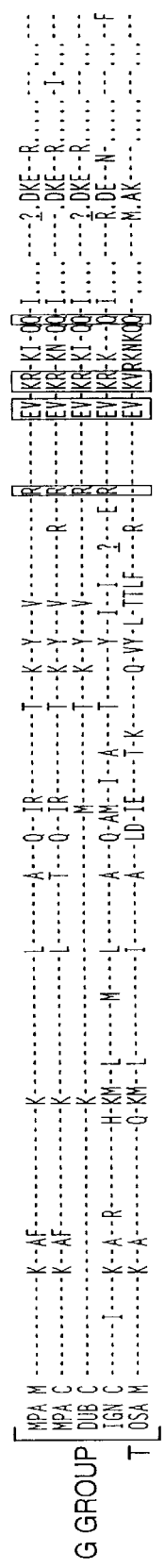
FIG. 3 shows the multiple alignment of the peptides originating from the p17 protein of HIV-1 from different viral isolates and their correlation with maternofoetal transmission.

FIG. 3 shows the alignment of 54 peptide sequences obtained.

Inasmuch as there was no cloning step, each sequence of isolates constitutes the consensus of the major variant sequences.

For 4 children and 8 mothers, the sequences of isolates were heterogeneous in respect of 1 to 8 localizations (amino acid designated ? in the sequences of FIG. 2).

For the other isolates, a single p17 sequence was observed.

Each sequence of isolates from a child is very close to that of the mother (0.5 to 2%), suggesting that the virus transmitted is not a minor variant.

The child's viral subtypes also appear in the isolates from the mother which have been analysed beforehand, in accordance with the results obtained on the direct sequencing of the V3–V5 env region and other studies in which subcloning of the env gene has been performed.

Furthermore, as in the case of the V3 loop, in which a low intrapatient variation is observed for children during the first month of life, p17 does not appear to vary during this period of time.

The peptide sequences of the isolates have been classified among the different HIV-1 subtypes A, B, G and D.

According to MYERS (Human retroviruses and AIDS compendium Los Alamos, N. Mex., 1994), some amino acids may be considered to be a signature of each subtype (FIG. 3 and FIG. 5).

This subdivision is almost identical to the clades of DNA sequences, with the exception of the unique isolate of subtype D.

This division into subtypes has enabled all the sequence variations due to subtypes to be eliminated. When the functional domains of all the p17 proteins sequenced are compared, no significant difference is apparent either in respect of the myristoylation site or in respect of the nuclear localization sites.

However, a specific variation group is observed at the p17 polymerization site (from amino acid 47 Asn to amino acid 59 Gln) and in the phosphorylation sites (amino acids 110–114, which are, respectively, Lys Ser Lys Gln Lys, Lys Ser Lys Lys Lys and Ile Ser Gln Gln Lys in subtypes A, B and G). The phosphorylation site of the tyrosine Y132 described by GALLAY et al. (Cell, 1995, 80, 379–388) is conserved in all the subtypes.

Two domains displaying considerable variability are observed between amino acids 75 and 95 and between amino acids 103 and 109.

The variations in the first region are not associated with the subtypes, neither are they associated with transmission.

Surprisingly, when the domain 103–109 is studied more precisely, especially in subtype B, the motif Lys Ile Glu Glu Glu Gln Asn appears consistently in all children to whom the virus has been transmitted.

Furthermore, this motif is constant in the isolates from transmitting mothers.

In contrast, among the 16 viruses not transmitted, only 8 possess the motif Lys Ile Glu Glu Gln Gln Asn.

Figure 4A:
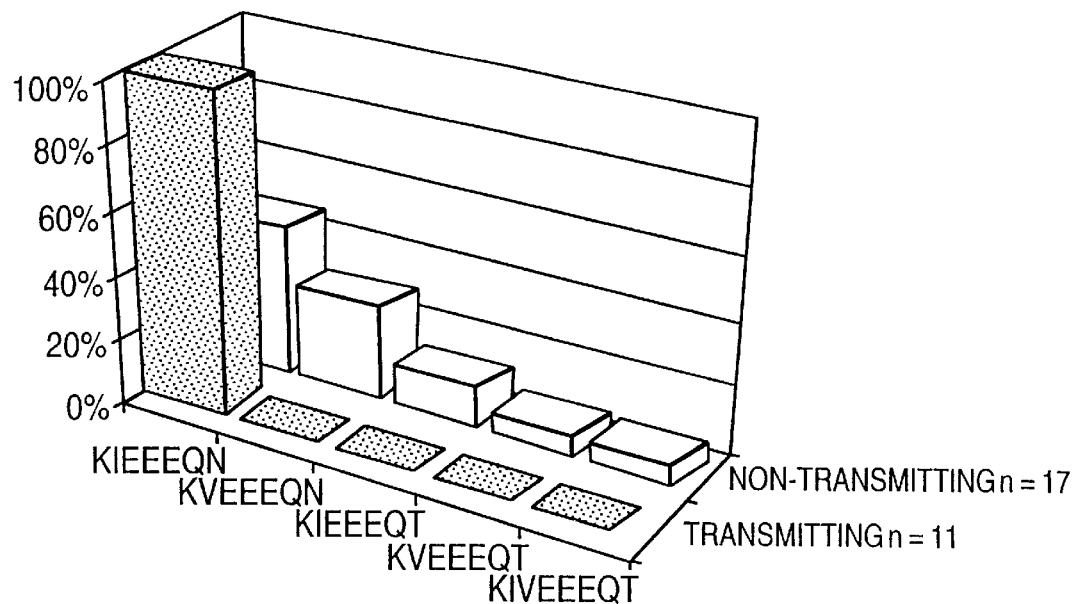
FIGS. 4A and 4B show the relationship between the peptide sequence 103–109 and the vertical transmission of HIV-1 in subtype B.
Figure 4B:
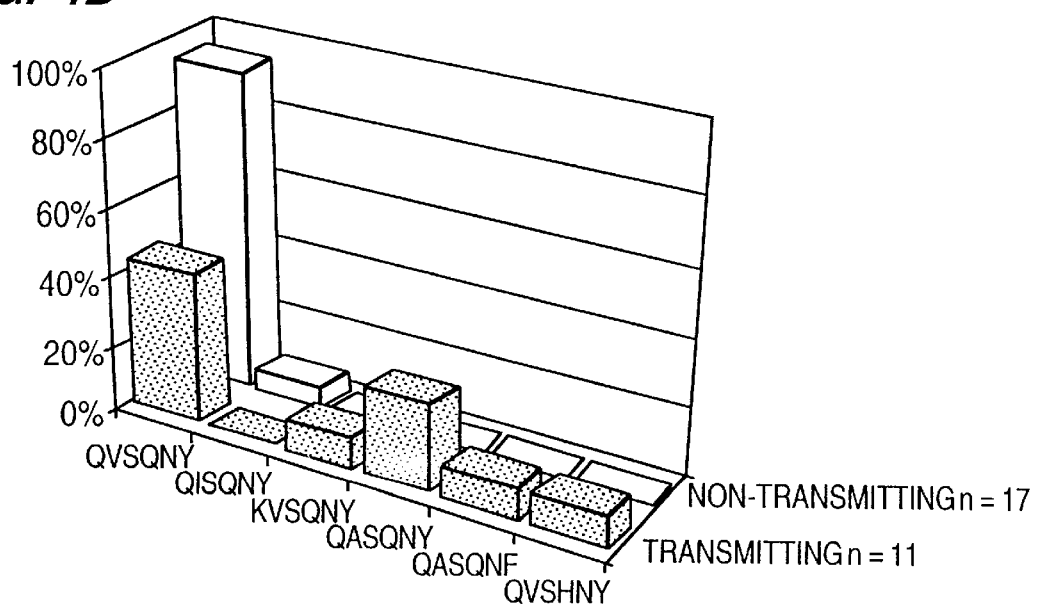

5 of the non-transmitted viruses have a motif Lys Val Glu Glu Glu Gln Asn, 2 a motif Lys Ile Glu Glu Glu Gln Asn and 1 a motif Lys Val Glu Glu Glu Gln Thr (FIG. 4A and FIG. 4B).

The N-terminal half of p17 is conserved overall in each subtype. In contrast, several domains of variability are observed in the C-terminal portion of p17.

These domains of variability and several variable amino acids have been compared in subgroup B, which constitutes the largest subgroup of the cohort studies.

These comparisons were carried out between the non-transmitting groups and the transmitting groups. These results are illustrated in FIG. 4A, which shows the relationship between the sequence 103–109 of the p17 protein of HIV-1 and the transmission observed in the child of a cohort of HIV-1 subgroup B-infected mothers. The percentage of each motif 103–109 is shown shaded for the non-transmitting mothers and in black for the transmitting mothers.

In particular, all the transmissible sequences comprise as sequence X2 X3 Glu X4 X5 X7 X7, the sequence Lys Ile Glu Glu Glu Gln Asn (motif KIEEQN) ($\chi^2$=p=0.0034), whereas the presence of a valine for X3 is associated significantly with a non-transmissible phenotype ($\chi^2$=p=0.014).

Table II below corresponds to a statistical analysis of the variable amino acids and motifs of the p17 protein of HIV-1 subtype B.

TABLE II

| Amino acids | Number in 11 transmitted isolates | Number in 17 nontransmitted isolates | $X^2$ | $X^2$ corrected for continuity |
|---|---|---|---|---|
| Arginine 30 | 6 | 8 | 0.6957 | 1 |
| Arginine 75 | 7 | 8 | 0.395 | 0.637 |
| Glutamic acid 83 | 9 | 7 | 0.0338 | 0.083 |
| Glutamic acid 102 | 8 | 14 | 0.1117 | 0.245 |
| KIEEEQM | 11 | 8 | 0.0034 | 0.012 |
| Valine 104 | 0 | 7 | 0.014 | 0.044 |
| Glycine 120 | 8 | 11 | 0.657 | 0.976 |
| QVSQMY | 5 | 16 | 0.0037 | 0.014 |

2 amino acids and 2 domains appear to be sufficient in themselves to discriminate between the non-transmitting group and the transmitting group:

1) The glutamic acid residue at position 93 is associated significantly with the transmitting phenotype ($\chi^2$ p=0.0338).
2) The first statistically significant domain for the analysis of transmission is the motif QVSQNY corresponding to the C-terminal fragment of the p17 protein; in particular, in subtype B, it is associated significantly with the non-transmitting group ($\chi^2$ p=0.0037). These results are illustrated in FIG. 4B, which shows the relationship between the C-terminal sequences of the HIV-1 p17 protein and the transmission of the virus in the same cohort of mothers. It emerges from these results that the motif QVSQNY is associated with an absence of transmission.
3) Depending on the presence of the motif Lys Ile Glu Glu Glu Gln Asn, there is a significant difference between the isolates from transmitting mothers and the isolates from non-transmitting mothers ($\chi^2$=p=0.0034).

Furthermore, the 6 transmitted viruses of subtype B possess the same peptide motif Lys Ile Glu Glu Glu Gln Asn.

4) In addition, the presence of the valine residue at position 104 appears to be associated with the non-transmitting phenotype ($\chi^2$=p=0.014).

Consequently, the method according to the invention which comprises a set of peptides makes it possible, in fact, to evaluate the risk of maternofoetal transmission of HIV-1 and, as a result, enables the certain and/or uncertain cases of transmission to be eliminated (FIG. 5).

EXAMPLE 4

Preparation of Control Antibodies

1) Preparation of peptides

The chemical synthesis of the target peptides is performed on a 433 synthesizer (Applied biosystem) using FMOC chemistry; the monitoring of synthesis is carried out by conductimetry and the peptides are purified by semi-preparative HPLC. 15 mg of each of the peptides may be produced with a purity of 98 to 99%.

Two residues (Tyr-Gly) were added to the N-terminal end for the purposes of synthesis.

6.7 mg of each of these peptides were coupled to 10 mg of KLH protein (BDB reagent). The various conjugates obtained are used to prepare specific antibodies.

2) Preparation of control antibodies

150 μg of each peptide as obtained in 1) are used to prepare specific IgY antibodies, by immunization of chickens by the company BioCytex-bioService (Marseilles, France) according to the following protocol:

immunization phase
   D1: Preimmune control on serum on or eggs
   Intramuscular injection of the antigen in Freund's complete adjuvant
   D10: Intramuscular injection of the antigen in Freund's complete adjuvant
   Collection of eggs from D11 to D19 and control of the immune response by the ELISA method
   D20: Intramuscular injection of the antigen in Freund's complete adjuvant
production phase
   From D21: collection of 6 to 7 eggs
   D28: Extraction of immunoglobulins Y
   Determination of the specific IgY concentration by the ELISA method
   Immune serum will also be drawn.

As emerges from the foregoing, the invention is in no way limited to those of its embodiments or modes of realization and application which have just been described more explicitly; it encompasses, on the contrary, all variants which may occur to a specialist in the field, without departing from the scope or the applicability of the present invention.

We claim:

1. A peptide comprising an amino acid sequence selected from the group consisting of SEQ ID No. 36 (DIA), SEQ ID No. 37 (MAM), SEQ ID No. 38 (MOU), SEQ ID No. 39 (BAB), SEQ ID No. 40 (DOS), SEQ ID No. 41, (LAN), SEQ ID No. 42 (FRA), SEQ ID No. 43 (WAN), SEQ ID No. 46 (4501), SEQ ID No. 48 (CEL), SEQ ID No. 49 (SIW), SEQ ID No. 50 (MOE), SEQ ID No. 51 (GOB), SEQ ID No. 52 (MPA), SEQ ID No. 53 (IGN), and SEQ ID No. 54 (OSA).

2. An immunogenic composition comprising one or more peptides of claim 1.

3. The immunogenic composition of claim 2 further comprising a carrier.

4. The peptide of claim 1 wherein said amino acid sequence is selected from the group consisting of SEQ ID No. 48 (CEL), SEQ ID No. 50 (MOE), and SEQ ID No. 51 (GOB).

5. An immunogenic composition comprising one or more peptides of claim 4.

6. The immunogenic composition of claim 5 further comprising a carrier.

7. A purified and isolated peptide which consists of amino acids 6 through 12 of SEQ ID No. 44 (Lys Ile Glu Glu Glu Glu Gln Asn).

8. An immunogenic composition comprising the peptide of claim 7.

9. The immunogenic composition of claim 8 further comprising a carrier.

10. A purified and isolated peptide which consists of amino acids 6 through 12 of SEQ ID No. 47 (Lys Val Glu Glu Glu Gln Asn).

11. An immunogenic composition comprising the peptide of claim 10.

12. The immunogenic composition of claim 11 further comprising a carrier.

13. A peptide sequence selected from the group consisting of SEQ ID No. 36 (DIA), SEQ ID No. 37 (MAM), SEQ ID NO. 38 (MOU), SEQ ID No. 39 (BAB), SEQ ID No. 40 (DOS), SEQ ID No. 41, (LAN), SEQ ID No. 42 (FRA), SEQ ID No. 43 (WAN), SEQ ID No. 44 (ABD), SEQ ID No. 45 (BOI), SEQ ID No. 46 (4501), SEQ ID No. 47 (HAR), SEQ ID No. 48 (CEL), SEQ ID No. 49 (SIW), SEQ ID No. 50 (MOE), SEQ ID No. 51 (GOB), SEQ ID No. 52 (MPA), SEQ ID No. 53 (IGN), SEQ ID No. 54 (OSA) and SEQ ID No. 55 (BOU).

14. A peptide consisting of seven consecutive amino acids wherein the seven consecutive amino acids are the consecutive amino acids at positions 6, 7, 8, 9, 10, 11 and 12 of the sequences selected from the group consisting of SEQ ID No. 36 (DIA), SEQ ID No. 37 (MAM), SEQ ID No. 38 (MOU), SEQ ID No. 39 (BAB), SEQ ID No. 40 (DOS), SEQ ID No. 41, (LAN), SEQ ID No. 42 (FRA), SEQ ID No. 43 (WAN), SEQ ID No. 44 (ABD), SEQ ID No. 45 (BOI), SEQ ID No. 46 (4501), SEQ ID No. 47 (HAR), SEQ ID No. 48 (CEL), SEQ ID No. 49 (SIW), SEQ ID No. 50 (MOE), SEQ ID No. 51 (GOB), SEQ ID No. 52 (MPA), SEQ ID No. 53 (IGN), SEQ ID No. 54 (OSA) and SEQ ID No. 55 (BOU).

15. An immunogenic composition comprising one or more peptides of claim 13 or claim 14.

16. The immunogenic composition of claim 15 further comprising a carrier.

* * * * *